United States Patent
Carpenter et al.

(10) Patent No.: US 6,796,957 B2
(45) Date of Patent: Sep. 28, 2004

(54) STERILE ASPIRATION/REINJECTION SYSTEMS

(75) Inventors: Kenneth W. Carpenter, La Jolla, CA (US); Michelle Fourmont, Carlsbad, CA (US); E. Thomas Malphus, La Jolla, CA (US); Kazuo Sasamine, Lemon Grove, CA (US); Hong Li, San Diego, CA (US)

(73) Assignee: Myocardial Therapeutics, Inc., La Jolla, CA (US)

( * ) Notice: Subject to any disclaimer, the term of this patent is extended or adjusted under 35 U.S.C. 154(b) by 238 days.

(21) Appl. No.: 10/004,525

(22) Filed: Oct. 23, 2001

(65) Prior Publication Data

US 2003/0069543 A1 Apr. 10, 2003

Related U.S. Application Data

(60) Provisional application No. 60/304,641, filed on Jul. 10, 2001, and provisional application No. 60/304,607, filed on Jul. 10, 2001.

(51) Int. Cl.[7] .............................................. A61M 31/00
(52) U.S. Cl. ..................... 604/93.01; 604/154; 604/131
(58) Field of Search .......................... 604/65–67, 156, 604/30–36, 82, 131, 93.01, 154, 155, 157, 315; 128/DIG. 1, DIG. 12, DIG. 13

(56) References Cited

U.S. PATENT DOCUMENTS

| | | | |
|---|---|---|---|
| 4,314,565 A | | 2/1982 | Lee |
| 4,319,568 A | * | 3/1982 | Tregoning .................. 604/67 |
| 4,430,079 A | * | 2/1984 | Thill et al. .................. 604/154 |
| 4,481,946 A | | 11/1984 | Altshuler et al. |
| 4,486,188 A | | 12/1984 | Altshuler et al. |
| 4,513,754 A | | 4/1985 | Lee |
| 4,630,616 A | | 12/1986 | Tretinyak |
| 4,664,128 A | | 5/1987 | Lee |
| 4,900,303 A | | 2/1990 | Lemelson |
| 5,257,632 A | | 11/1993 | Turkel et al. |
| 5,294,325 A | | 3/1994 | Liu |
| 5,331,972 A | | 7/1994 | Wadhwani et al. |
| 5,531,672 A | | 7/1996 | Lynn |
| 5,591,159 A | | 1/1997 | Taheri |
| 5,607,421 A | | 3/1997 | Jeevanandam et al. |
| 5,782,824 A | | 7/1998 | Abela et al. |
| 5,810,836 A | | 9/1998 | Hussein et al. |
| 5,840,059 A | | 11/1998 | March et al. |
| 5,876,373 A | | 3/1999 | Giba et al. |

(List continued on next page.)

FOREIGN PATENT DOCUMENTS

| | | |
|---|---|---|
| WO | WO 01/24851 A1 | 4/2001 |
| WO | WO 01/26706 A2 | 4/2001 |

*Primary Examiner*—Manuel Mendez
(74) *Attorney, Agent, or Firm*—Gray Cary Ware & Freidenrich, LLP

(57) ABSTRACT

The invention provides systems containing a sterile container for aspiration, filtering, treating and reinjection into a subject of a bodily fluid in a sterile environment. The systems are particularly designed to facilitate transfection of cells within the sterile container by gene therapy molecules and reinjection of the transfected cells into the donor at controlled depth in precisely controlled volumes such as is useful for revascularization of ischemic cardiac tissue. For injection, a pressure actuator, preferably hand-held, applies force to liquids held within the sterile container in precisely controlled increments, thereby expressing liquids through a hollow needle or injection catheter in precisely controlled microvolumes. The invention systems include a hand-held injection device with audible cues that correspond to an operator-selected injection volume and/or audible cues that correspond to needle penetration depth selected by the operator.

45 Claims, 17 Drawing Sheets

U.S. PATENT DOCUMENTS

| | | |
|---|---|---|
| 5,885,272 A | 3/1999 | Aita et al. |
| 5,904,670 A | 5/1999 | Schreiner |
| 5,968,059 A | 10/1999 | Ellis et al. |
| 5,980,548 A | 11/1999 | Evans et al. |
| 5,993,421 A * | 11/1999 | Kriesel ..................... 604/132 |
| 6,090,064 A | 7/2000 | Reilly et al. |
| 6,117,130 A | 9/2000 | Kung |
| 6,126,654 A | 10/2000 | Giba et al. |
| 6,171,251 B1 | 1/2001 | Mueller et al. |
| 6,203,556 B1 | 3/2001 | Evans et al. |
| 6,217,554 B1 | 4/2001 | Green |
| 6,224,584 B1 | 5/2001 | March et al. |
| 6,226,554 B1 | 5/2001 | Tu et al. |
| 6,360,784 B1 * | 3/2002 | Philippens et al. ............ 141/2 |
| 6,387,077 B1 * | 5/2002 | Klibanov et al. ........... 604/181 |
| 6,403,056 B1 * | 6/2002 | Unger ..................... 424/9.51 |

\* cited by examiner

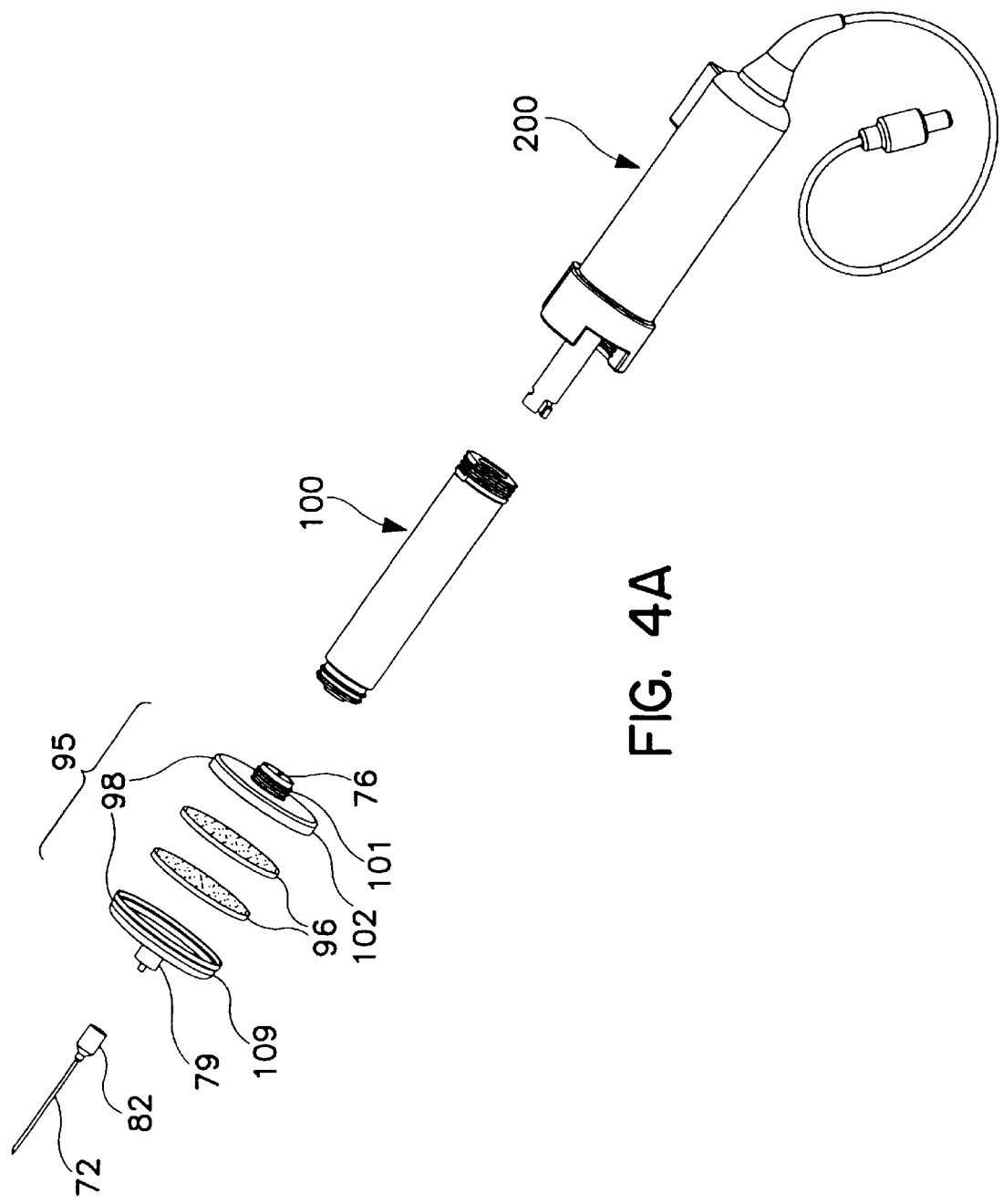

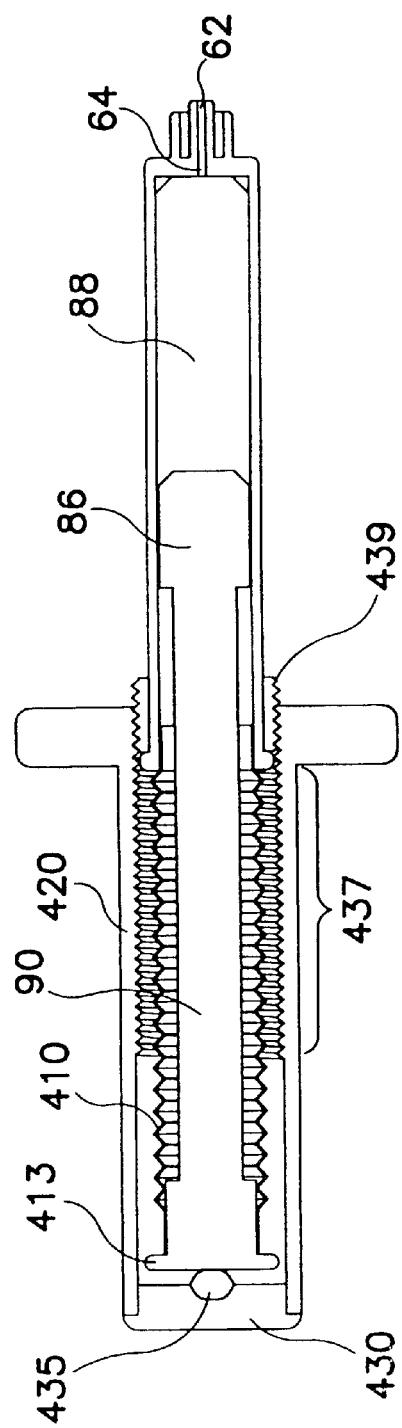
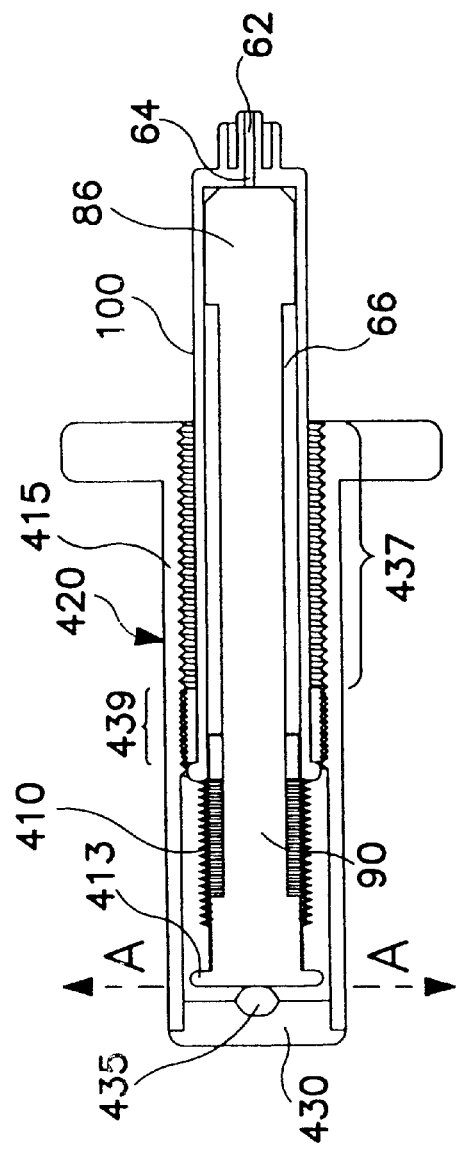
FIG. 11A
FIG. 11B

STERILE ASPIRATION/REINJECTION SYSTEMS

This application claims priority under 35 U.S.C. § 119(e) of U.S. Provisional Application Serial No. 60/304,641, filed Jul. 10, 2001, and U.S. Provisional Application Serial No. 60/304,607, filed Jul. 10, 2001, the entire contents of which are incorporated herein by reference.

This application is related to U.S. application Ser. No. 10/000,786 entitled "FLEXIBLE TISSUE INJECTION CATHETERS WITH CONTROLLED DEPTH PENETRATION"; U.S. application Ser. No. 60/304,607 entitled METHODS FOR CONTROLLED DEPTH INJECTIONS INTO INTERIOR BODY CAVITIES, and U.S. application Ser. No. 10/004,525 entitled METHODS FOR STERILE ASPIRATION/REINJECTION OF BODILY FLUID, filed on even date herewith, the entire contents of each of which is incorporated herein by reference.

BACKGROUND OF THE INVENTION

1. Field of the Invention

The present invention relates generally to medical systems and procedures and more particularly to devices and methods of their use for injection of a therapeutic agent into the surface of an interior body cavity of a living being.

2. Background Information

Market expansion in cardiovascular and cardiothoracic surgery in past years has largely been driven by increases in open-heart surgical bypass procedures, but new opportunities for growth will come from products associated with least-invasive procedures. The positive outcomes seen thus far with these techniques, accompanied by continued physician acceptance, will lead to a gradual erosion of the market for traditional open-heart surgery.

Driven by capitation and cost-cutting measures associated with managed care, these evolving techniques and procedures not only hold the promise of reduced trauma to patients, but also reduce the significant costs associated with traditional open-heart surgery. Markets for least-invasive invasive approaches to cardiothoracic surgery, including equipment and disposables, are predicted to grow at tremendous rates for the next twenty years.

Within the past few years, an increasing number of centers worldwide have begun performing revolutionary techniques, such as beating-heart coronary artery bypass and laser transmyocardial revascularization (TMR). These developing procedures offer the potential of expanding the size of the eligible patient base by providing significantly reduced patient trauma and lower costs, as well as providing a viable alternative to patients unable to undergo open heart surgery.

Bone marrow cells and liquid aspirate are believed to be the source of angiogenic peptides known as growth factors. In addition, recent studies have shown that bone marrow cells include stem cells that differentiate into angioblasts. Angiogenesis represents the postnatal formation of new blood vessels by sprouting from existing capillaries or venules. During angiogenesis, endothelial cells are activated from a quiescent microvasculature (turnover of thousands of days) to undergo rapid proliferation (turnover of a few days).

In one technique currently in clinical stage testing, autologous bone marrow cells are transplanted into the heart to restore heart function. In one such procedure, autologous bone marrow cells obtained by aspiration from the patient's hipbone are transplanted into transventricular scar tissue for differentiation into cardiomyocytes to restore myocardial function (S. Tomita, et al., *Circulation* 100:19 Suppl II 247–56, 1999). In another technique, autologous bone marrow cells are harvested and transplanted into an ischemic limb or ischemic cardiac tissue as a source of angiogenic growth factors, such as VEGF (A. Sasame, et al., *Jpn Heart J*, Mar 40:2 165–78, 1999).

To perform such techniques, various types of needles and needle assemblies used for bone marrow biopsy, aspiration, and transplant have been proposed and are currently being used. Many such bone marrow harvesting devices include a cannula, stylet with cutting tip, or trocar that can be used to cut a bone marrow core sample. On the other hand, devices designed for withdrawal of liquid bone marrow aspirate typically comprise a large gauge hollow needle attached to a device for creating a negative pressure to aspirate the liquid bone marrow.

Current procedures used for harvesting, purification and reinjection of autologous bone marrow cells may require sedation of the patient for a period of three to four hours while the bone marrow aspirate is prepared for reinjection. In addition, the present procedure involves great risk of infection for the subject because the harvested bone marrow material is routinely aspirated in an operating or recovery room and then transferred after aspiration to a laboratory where the aspirate is placed into a centrifuge for gravity separation of bone marrow cells from the aspirate. In many cases the bone marrow aspirate is transferred into a specially designed centrifuge tube for the gravity separation. The separated bone marrow cells are then removed from the centrifuge tube into a syringe and transferred back to the recovery room or operating room for reinjection into the patient. Thus, the bone marrow aspirate is handled under potentially non-sterile conditions and reinjected into the patient as a potentially non-sterile preparation.

Generally, the processed cells are injected by catheter into the ischemic site where reperfusion is required. For example, it is known to deliver bone marrow cells by pericardial catheter into the subject's myocardium to stimulate angiogenesis as a means of reperfusing ischemic tissue with collaterally developed capillaries. However, prior art methods for preparation and injection of non-sterile bone marrow aspirate risk introduction of pathogens with consequent increased risk of infection for the patient.

Angiogenic peptides like VEGF (vascular endothelial growth factor) and bFGF (basic fibroblast growth factor) have also entered clinical trials for treatment of coronary artery disease. Attempts are being made to devise clinically relevant means of delivery and to effect site-specific delivery of these peptides to ischemic tissue, such as heart muscle, in order to limit systemic side effects. Typically cDNA encoding the therapeutic peptide is either directly injected into the myocardium or introduced for delivery into a replication-deficient adenovirus carrying the cDNA to effect development of collateral arteries in a subject suffering progressive coronary occlusion.

Recently, various publications have postulated on the uses of gene transfer for the treatment or prevention of disease, including heart disease. See, for example, Mazur et al., "Coronary Restenosis and Gene Therapy," Molecular and Cellular Pharmacology, 21:104–111, 1994; French, "Gene Transfer and Cardiovascular Disorders," Herz 18:222–229, 1993; Williams, "Prospects for Gene Therapy of Ischemic Heart Disease," American Journal of Medical Sciences 306:129–136, 1993; Schneider and French, "The Advent of Adenovirus: Gene Therapy for Cardiovascular Disease,"

Circulation 88:1937–1942, 1993. Another publication, Leiden et al, International Patent Application Number PCT/US93/11133, entitled "Adenovirus-Mediated Gene Transfer to Cardiac and Vascular Smooth Muscle," reports on the use of adenovirus-mediated gene transfer for the purpose of regulating function in cardiac vascular smooth muscle cells. Leiden et al. states that a recombinant adenovirus comprising a DNA sequence that encodes a gene product can be delivered to a cardiac or vascular smooth muscle cell and the cell maintained until that gene product is expressed. According to Leiden et al., muscle cell function is regulated by altering the transcription of genes and changes in the production of a gene transcription product, such as a polynucleotide or polypeptide. Leiden et al. describe a gene transfer method comprising obtaining an adenoviral construct containing a gene product by co-transfecting a gene product-inserted replication deficient adenovirus type 5 (with the CMV promoter) into 293 cells together with a plasmid carrying a complete adenovirus genome, such as plasmid JM17; propagating the resulting adenoviral construct in 293 cells; and delivering the adenoviral construct to cardiac muscle or vascular smooth muscle cells by directly injecting the vector into the cells.

There are impediments to successful gene transfer to the heart using adenovirus vectors. For example, the insertion of a transgene into a rapidly dividing cell population will result in substantially reduced duration of transgene expression. Examples of such cells include endothelial cells, which make up the inner layer of all blood vessels, and fibroblasts, which are dispersed throughout the heart. Targeting the transgene so that only the desired cells will receive and express the transgene, and the transgene will not be systemically distributed, are also critically important considerations. If this is not accomplished, systemic expression of the transgene and problems attendant thereto can result. For example, inflammatory infiltrates have been documented after adenovirus-mediated gene transfer in liver (Yang, et al. *Proc. Natl. Acad. Sci.* (*U.S.A.*) 91:4407, 1994). Finally, with regard to adenovirus-mediated gene transfer of FGF-5 for the in vivo stimulation of angiogenesis, it is known that in some cases the injected viral material can induce serious, often life-threatening cardiac arrhythmias.

It is also known to transfect autologous bone marrow cells obtained as described above with such adenovirus transformed with cDNA encoding such therapeutic peptides for in vivo expression of the angiogenic peptides at the ischemic site. However, the handling of adenovirus vectors is generally considered a risk to the medical team members responsible for their preparing and handling and/or their injection into patients. For this reason, current practice is to prepare the vectors and transform the bone marrow cells "under the hood" to curtail possible escape of the adenovirus, thus requiring transport of the bone marrow to a laboratory for transfection and then return to the patient for injection of the transfected cells.

Least-invasive methods of treatment wherein a therapeutic agent, such as an angiogenic agent, is injected by catheter into an interior body site also raise the difficult problem of controlling the location injected as well as the depth and amount of therapeutic agent injected. For example, the amount of extraneously introduced angiogenic growth factor, such as VEGF, that can be tolerated by the subject is very small. At high doses VEGF is known to cause a drop in blood pressure. Over dosage has proven to be fatal in at least one clinical trial. Thus strict control of the amount of growth factor delivered is of great importance. In addition, since the delivery site is located along the surface of an interior body cavity, such as the myocardium, a deflectable intravascular catheter with an infusion needle is customarily used, but it is difficult to control the location and angle of penetration of the myocardium to effect uniformly spaced delivery of uniform amounts of the therapeutic agent.

In some cases, controlling the depth of needle penetration is complicated by the tendency of prior art steerable infusion catheters to withdraw the needle into the catheter when the catheter is deflected to approach the wall of an internal organ. In compensation for needle withdrawal, it is current practice to advance the needle from the tip of the catheter an extra distance. In some cases, where the catheter is advanced into the pericardial space to deliver a therapeutic fluid into the myocardium, the needle has actually punctured the wall of the heart, by over penetration with the result that the therapeutic fluid is not introduced into the myocardium at all.

Many therapeutic substances other than angiogenic agents are also introduced into the surface of interior body cavities. For example, the reverse of angiogenesis is practiced for a number of therapeutic purposes, such as the prevention of restenosis following a reperfusion procedure or in treatment of diabetic retinopathy and various types of cancer. In anti-restenosis, the growth of new blood vessels is blocked or curbed and the formation of new tissue (e.g., a growing tumor, neointima on the surface of a stent or vascular prosthesis, etc.) is limited or eliminated by introduction of "reverse angiogenesis" agents, such as angiostatin, endostatin or, antarin, a locally administered mitotoxin that inhibits cell proliferation into the tissue.

Thus, there is a need in the art for new and better equipment for use in handling and treating autologous bone marrow and for controlled delivery of fluid containing cells, nucleic acid encoding therapeutic peptides, and the like, into interior body cavities, especially into the vasculature and the interior or exterior of the heart to induce or curtail angiogenesis.

In particular, there is a need in the art for a sterile closed system aspiration/injection unit for bedside use that can be used to aspirate bone marrow fluids, treat the fluids in a sterile environment, and reinject the treated bone marrow aspirate into a subject in need of bone marrow treatment. The present invention satisfies these needs and provides additional advantages.

SUMMARY OF THE INVENTION

The present invention solves many of the problems in the art by providing sterile container systems for delivering repeated precisely controlled volumes of a liquid therefrom in a sterile condition. The invention systems comprise in liquid-tight arrangement a liquid-tight housing with an opening of reduced size relative to the housing; wherein the interior of the housing is maintained in a sterile condition and has a maximum internal volume in the range of about 3 ml to about 70 ml; a self-sealing puncturable sterile barrier covering the opening for receiving a hollow needle cannula, and a pressure actuator in liquid-tight connection with the interior of the housing. The pressure actuator repeatedly exerts a positive pressure on liquid in the interior of the housing so as to repeatedly expel a precisely controlled volume of the liquid therefrom via the opening without septic contamination of the liquid and without uncontrolled loss of liquid therefrom.

In another embodiment, the present invention provides filter assemblies for aspiration and filtering of a bodily liquid containing undesired components. The invention filter assemblies comprise in co-axial liquid-tight arrangement one or more replaceable filters with pores sized to filter out the undesired components from the liquid and a filter receptacle having at least a distal part and a proximal part which parts engage to cooperatively form a liquid-tight enclosure for the one or more filters, wherein the distal part of the filter receptacle attaches to the hub of the aspiration needle; a hollow needle cannula attached to the exterior of the proximal part of the filter receptacle; and a liquid-tight liquid connector attached to the exterior of the distal side of the filter receptacle. Components of the invention filter assembly may be releasably attached.

In another embodiment, the present invention provides aspiration/injection systems for aspiration and filtering of a bodily liquid containing undesired components. In this embodiment, the invention aspiration/injection systems comprise in co-axial liquid-tight arrangement:

a) an invention sterile container;
b) an invention flow-through filter assembly;
c) an aspiration needle with hub attached to the fluid connector;
d) an aspiration syringe with moveable plunger in liquid connection with the hub of the aspiration needle; and
e) a three-way flow diverter;

wherein the needle cannula of the filter assembly punctures the sterile barrier of the sterile container and wherein the flow diverter is positioned to divert liquids aspirated through the needle into the syringe and to divert liquids ejected from the syringe into the sterile container through the flow-through filter assembly.

In another embodiment, the present invention provides sterile containers for treating bodily liquid containing cells. In this embodiment, the invention sterile containers comprise in co-axial arrangement:

a housing having a cylindrical portion and a distal portion of reduced diameter;
a distal opening;
a puncturable, self-sealing sterile barrier covering the distal opening;
one or more piston ring-like stops fixedly mounted circumferentially around an interior wall of the cylindrical portion of the housing;
a piston-like plunger having a domed head portion shaped to conform to the interior of the distal end of the housing; wherein the plunger is liquid-tightly and moveably mounted within the cylindrical portion of the housing so that the stroke of the plunger is defined by abutment of the head portion against the distal opening and against a stop; and
a proximally extending plunger handle for moving the plunger within the cylindrical portion of the housing;
wherein the sterile barrier, the cylindrical portion of the housing, and the exterior of the domed head portion of the plunger form an expandable and compressible sterile chamber.

In yet another embodiment, the present invention provides sterile systems for injection of one or more precisely controlled volumes of a liquid. The invention sterile injection system comprises:

a) an invention sterile container, said container comprising in co-axial arrangement:
    a housing having a cylindrical portion and a distal portion of reduced diameter;
    a distal opening;
    a puncturable, self-sealing sterile barrier covering the distal opening;
    one or more piston ring-like stops fixedly mounted circumferentially around an interior wall of the cylindrical portion of the housing;
    a piston-like plunger having a domed head portion shaped to conform to the interior of the distal end of the housing; wherein the plunger is liquid-tightly and moveably mounted within the cylindrical portion of the housing so that the stroke of the plunger is defined by abutment of the head portion against the distal opening and against a stop; and
    a plunger handle for moving the plunger within the cylindrical portion of the housing;
    wherein the sterile barrier, the cylindrical portion of the housing, and the exterior of the domed head portion of the plunger form an expandable and compressible sterile chamber;
b) a hollow needle in fluid communication with the sterile chamber via the sterile barrier of the sterile container; and
(c) a pressure actuator operationally coupled to the plunger handle of the sterile container;
wherein the pressure actuator exerts a positive pressure on liquid in the sterile chamber so as to expel liquids therefrom in a controlled volume by distal movement of the container plunger one or more precisely controlled longitudinal distances.

In still another embodiment, the present invention provides hand-operated injection systems for injection of a precisely controlled volume of a therapeutic fluid in a sterile condition. In this embodiment, the invention hand-operated injection systems comprise in sterile, fluid-tight communication:

a) a sterile container, said sterile container comprising:
    an elongated liquid-tight housing with an opening of reduced size relative to the housing; wherein the interior surface the housing defines a sterile fluid chamber
    a self-sealing puncturable sterile barrier covering the opening for receiving a hollow needle cannula, and
    a hand-operated plunger constructed and arranged within said chamber for reciprocal motion within the chamber;
b) an injection syringe, said injection syringe comprising:
    an elongated barrel having an inner surface defining a fluid chamber and a distal fluid port,
    a plunger constructed and arranged within said fluid chamber for reciprocal motion within the fluid chamber;
c) an adjustable plunger arrester positioned with respect to the syringe plunger so as to precisely and adjustably control proximal travel of the plunger;
d) a needle connector comprising a hollow needle cannula and connector for attachment of a hollow injection needle; and
e) one way liquid flow valves for directing discrete liquid flow from the opening of the sterile container via the puncturable, sterile barrier into the distal fluid port of the syringe and from the fluid port of the syringe into the needle connector;
wherein the controlled distance of proximal travel of the plunger allowed by the plunger arrester precisely controls the volume of the sterile fluid expelled from the system upon depression of the syringe plunger.

In still another embodiment, the present invention provides hand-operated injection systems for injection of a precisely controlled volume of a therapeutic fluid in a sterile condition that comprise in sterile, fluid-tight communication:

a) a fluid-tight sterile container, said sterile container comprising:
   an elongated liquid-tight housing with a distal opening of reduced size relative to the housing; wherein the interior surface the housing defines a sterile fluid chamber having a maximum internal volume in the range from about 3 ml to about 30 ml;
   a self-sealing puncturable sterile barrier covering the opening for receiving a hollow needle cannula,
   a plunger constructed and arranged within said chamber for reciprocal motion within the chamber, said plunger comprising a distal head and proximal plunger handle extending from the proximal end of the housing;
   a fluid-tight seal moveably mounted on the extending portion of the plunger handle so as to maintain a seal of the fluid chamber upon reciprocal motion of the plunger, and
b) an elongated holder for grasping by the operator, said holder comprising
   an elongated side portion,
   an opening at the distal end, and
   an end piece closing the proximal end
   wherein the holder is shaped for rotatable plunger-first reception of the sterile container and wherein each rotation or partial rotation of the holder about the sterile container causes the plunger to expel a precisely controlled volume of a fluid contained in the sterile chamber, and
c) a signaling mechanism formed by cooperative interaction of the holder and the plunger handle during the rotation generates a sensible signal;
wherein the signal advises the operator how many of the precisely controlled volumes of the fluid have been expelled as a result of the operator causing the rotation of the holder about the sterile container.

In another embodiment, the present invention provides systems for delivery of a therapeutic fluid with controlled depth penetration that comprise:

a) an injection catheter comprising:
   an elongate hollow catheter body having a proximal end and a distal end with a flexible portion at the distal tip thereof, said catheter body being sized and constructed to be advanced intravascularly into an interior body cavity of a subject;
   a hollow needle housed throughout the catheter body, said needle having a distal portion with a sharp tip and a proximal portion, wherein the distal portion extends from the distal end of the catheter body; and
   an operator-controlled adjustable needle stop fixedly attached to distal portion of the needle wherein one or more precisely controlled increments of the distal tip of the needle are exposed by the operator advancing the needle distally through a series of positions within the needle stop or by rotating the needle stop about the needle, and wherein the needle stop provides a sensible signal to the operator that indicates how many of the precisely controlled increments of the distal tip have been extended from within the needle stop by the operator and wherein the depth of needle penetration is controlled by the length of the distal tip of the needle exposed by the operator; and
b) an invention hand-operated injector system, wherein the proximal end of the injection needle is in fluid communication with the sterile chamber of the sterile container via the sterile barrier.

BRIEF DESCRIPTION OF THE DRAWINGS

FIG. 1A shows an exterior view and FIG. 1B shows a longitudinal cross-section of the interior of the sterile container.

FIGS. 4A and 4B are perspective drawings showing exploded views of an embodiment of the invention injection systems that includes an injection needle, a filter assembly, an invention sterile container, and a motor driven pressure actuator.

FIGS. 11A and 11B are drawings showing longitudinal cross-sections of the hand-held injection system of FIG. 10 with the sterile container received into the holder. In FIG. 11A, the plunger handle is in an extended position to accommodate a volume of fluid in the sterile chamber. In FIG. 11B, the plunger has been driven to its proximal-most position so as to reduce the volume of the sterile chamber to zero.

DETAILED DESCRIPTION OF THE INVENTION

Figure 1A:
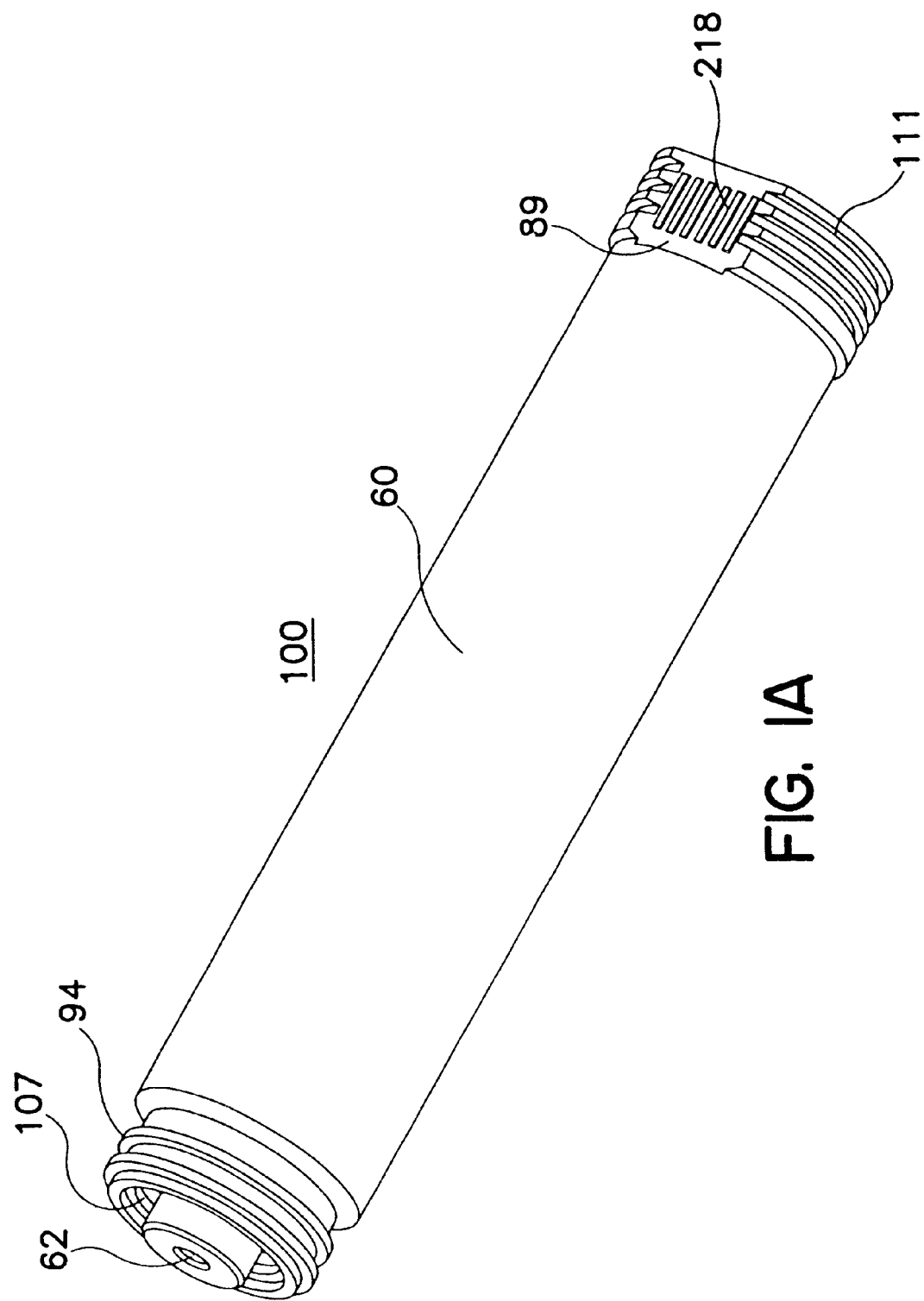
FIGS. 1A and 1B are drawings showing views of the invention sterile container with moveable plunger therein.

The present invention relates generally to self-contained apparatus for aspiration and filtering of a bodily fluid containing undesired components and for treatment of the bodily fluids in a sterile environment in preparation for reinjection of the treated aspirate into a subject in need thereof, for example into an autologous donor. Although the invention is described as particularly useful for aspiration, filtering and treatment of bone marrow fluids in a self-contained, sterile environment, the apparatus and methods of the present invention may be used to aspirate and treat other bodily fluids as well, for example, blood.

In one embodiment according to the present invention, there are provided sterile containers for receiving and/or treating bodily fluid containing cells, such as bone marrow liquids, which contain both bone marrow cells and blood cells of various types. The invention sterile container comprises a liquid-tight housing with an opening of reduced size relative to the housing, a self-sealing puncturable sterile barrier covering the opening and a pressure actuator in fluid-tight connection with the interior of the housing for establishing within or introducing into the sterile confines of the fluid-tight housing a positive or negative pressure sufficient to aspirate liquids into the sterile confines of the housing or express liquids from the housing without uncontrolled loss of fluids from the housing via the pressure actuator. The sterile container must be sufficiently airtight that the pressure actuator can establish a partial vacuum within the sterile container for aspiration of fluids. Any type of vacuum source can be attached to the pressure actuator for this purpose. Alternatively, a partial vacuum can be established within the housing by withdrawing a plunger-type pressure actuator where there is a seal provided between the pressure actuator and the housing sufficient for this purpose. For expression of fluids from the sterile container, air pressure applied to liquid contents of the sterile container via the pressure actuator can be used to express fluids therefrom. Alternatively, since liquids are incompressible, the pressure actuator can be designed so as apply mechanical force to liquids held within the container, thereby expressing liquids through a hollow needle cannula inserted through the sterile barrier at the opening of the sterile container.

The puncturable and self-resealing sterile barrier (e.g., an elastomeric septum, a membrane, and the like) is readily penetrated by a needle, and is self-sealing to maintain a sterile condition within the housing of the sterile container when the puncturing needle is removed. Liquids can be aspirated into the sterile container through a hollow needle cannula thrust through the elastomeric septum to give entry into the sterile confines of the container housing when the pressure actuator is used to establish a negative pressure within the sterile housing. Similarly, liquids can be ejected therefrom via a needle placed through the sterile barrier when the pressure actuator is used to establish a positive pressure on liquids held within the sterile housing.

The housing of the sterile container can be made of any convenient material and can have any convenient shape. For example, the cross-sectional shape of the housing can be ellipsoid, octagonal, square, and the like, or the housing can take the form of a collapsible and/or inflatable bladder. The sterile container can itself be housed within a rigid canister to provide rigidity, for ease of handling, or to prevent direct handling of the sterile container. Preferably the canister is composed of a clear material with a smooth finish, e.g., a polycarbonate, so that an operator can see through the canister.

The pressure actuator associated with the sterile container can comprise any type of suction or pressure source, motorized pump, and the like, and preferably the pressure actuator provides adjustable pressure so that the volume of fluids drawn into or ejected from the sterile container can be exactly controlled even when the volumes are as small as microliters, for example wherein the volume is from about 0.1 ml to about 3.0 ml per expulsion. Most importantly, the pressure actuator provides controlled pressure on fluid in the sterile container so that such a precisely controlled fixed volume of fluid can be repeatedly ejected from the sterile container in a sterile condition. While in the container, the liquid is maintained in a sterile condition so that the liquid aspirated into the sterile container can be stored or treated while in the sterile container, for example by therapeutic agents preloaded (e.g., prepackaged) in the sterile container, and then reinjected into a subject in a sterile condition. Examples of pressure actuators that can be used in the invention sterile container assemblies include numerous syringe drug infusion pumps such as the ASENA® Infusion System from Alaris Medical Systems or the MULTI-PHASER® Programmable Syringe Pump from Yale Apparatus, as well as the motorized pressure actuator described in detail herein.

The opening of the sterile container is preferably provided with a fluid-tight connector, such as a luer lock or other fluid connector as is known in the art, for attachment of a hollow needle to the opening of the sterile container. For injection into a subject of fluids expressed from the sterile container, the fluid connector may further comprise a hollow needle that is sharp on both ends such that one end of the hollow needle cannula pierces the sterile barrier at the opening of the sterile container and the other end of the needle is used as a hypodermic needle to inject fluids expressed by the pressure actuator the sterile container into a subject. Alternatively, the fluid connector can comprise any type of flow-through needle assembly that provides on one end a needle cannula to pierce the sterile barrier of the sterile container and on the other end an injection needle for injection of fluids expressed from the sterile container into a subject.

The invention sterile container is arranged into various assemblages with additional components of the invention sterile aspiration/reinjection system, all of which releasably fit together in fluid tight fashion. Each assemblage, as described below, is specialized for performance of different functions or steps of the methods of aspirating, treating and reinjection of autologous fluids into a subject. For example, the components may releasably engage by friction fit, by screwing together, by a fitting together to form a luer lock, and the like. For example, a recess in the hub of the aspiration needle preferably provides a female luer connection and the proximal end of the filter receptacle provides a male luer connection for releasably attaching the aspiration syringe to the hub 82 of aspiration needle 72. The distal part and the proximal part of the filter receptacle may likewise releasably engage by friction fit, by screwing together, by a luer lock, or the like. In one embodiment, the distal and proximal parts of the receptacle are threaded so as to screw together. In another embodiment, wherein the filter assembly is disposable, the proximal and distal parts of the filter receptacle can be made of a light weight plastic and bonded or fused together with the filters inside.

The various components of the invention sterile aspiration/reinjection system will now be described in detail with reference to the Figures herein.

Figure 1B:
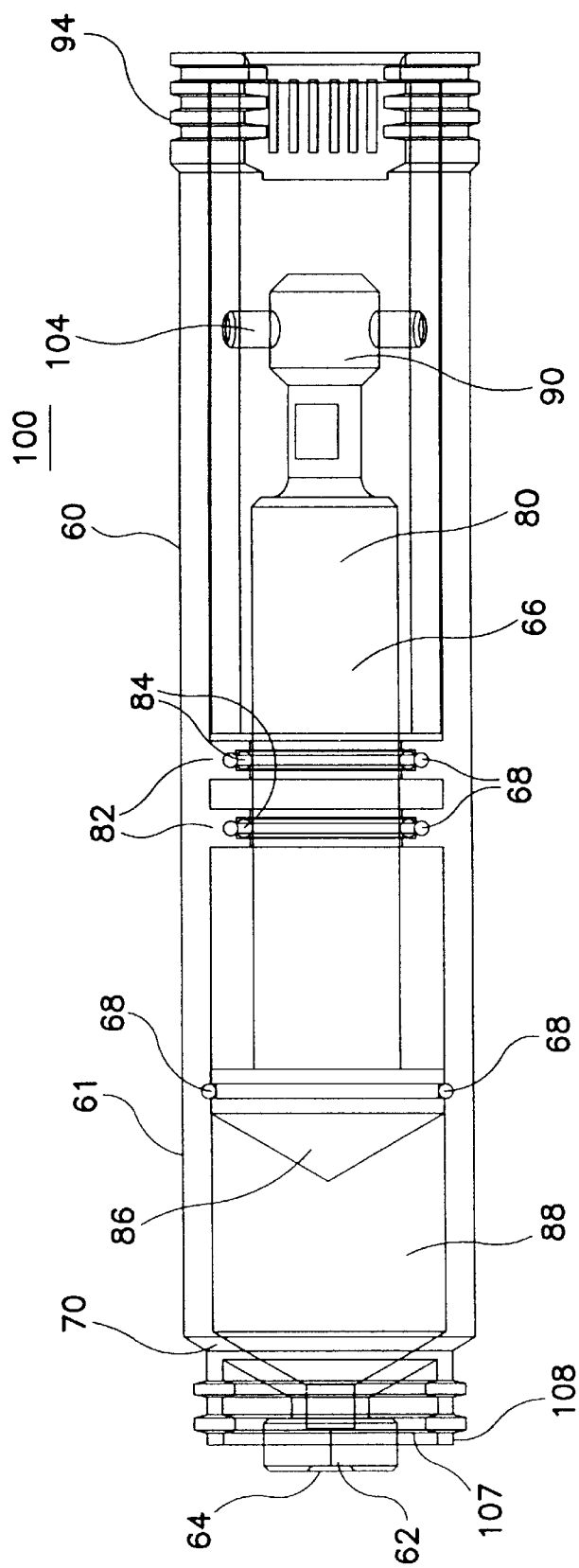

One embodiment of the invention sterile container 100 is shown in FIGS. 1A and 1B. The preferred sterile container comprises in co-axial arrangement a housing 60 having a cylindrical portion 61 with a distal portion of reduced diameter 70. Opening 62, located at the distal end of the cylindrical housing 60, also has a reduced diameter relative to the cylindrical portion 61 of housing 60 and is plugged or covered with a puncturable, self-sealing sterile barrier 64. The pressure actuator is shown as a piston-like plunger 66 that is circular in cross-section and fluid-tightly and moveably mounted within housing 60. The plunger is provided with a cylindrical portion 80 and a domed head portion 86 shaped to conform to the interior of the reduced diameter distal end of housing 60. A handle portion 90 at the proximal end of the plunger (shown as an extension of the cylindrical portion 70 with a slightly reduced diameter) is used to move the plunger head within the cylindrical portion 61 of the housing. In this embodiment, the proximal portion of sterile container housing 60 serves as a guide to position plunger 66 co-axially during movement of the plunger. Preferably, a lip 108 extends around opening 62 at the distal end of the sterile container 100 and is provided with internal threads 107 and external threads 111 for releasable fluid-tight attachment of the container to an invention filter assembly 95, needle adapter 97, or catheter.

As shown in longitudinal cross section in FIG. 1B, the plunger head 86 has a larger diameter than the cylindrical portion 61 of the plunger 66 so that proximal movement of the plunger is limited by the plunger head 86 abutting against the one or more piston ring-like stops 82 fixedly mounted circumferentially around an interior wall of the cylindrical portion 61 of housing 60. The piston ring-like stops 82 preferably additionally have seals 68, such as O-ring gaskets, at the point of contact between the stops and the cylindrical portion 80 of the plunger to form a fluid-tight seal that prevents blow-by of liquids from the sterile chamber. Preferably, the periphery of the plunger head 86 is also provided with sealing members 68, such as bushings, gaskets or O-rings, at the point of contact with the interior wall of the housing. The head portion 86 of the plunger 66 may also have one or more gaskets or seals 68 circumferentially attached thereto to provide a liquid-tight seal between the interior wall of the housing and the head portion of the plunger. As shown in FIG. 1B, the face of each stop 82 is provided with a groove 84 into which is fitted an O-ring friction seal 68 that contacts the surface of the cylindrical portion 80 of the plunger to facilitate liquid-tight (and sterile) fitting and movement of the plunger 66 within the housing 60 of the sterile container 100.

The sterile barrier 64, the interior wall of the housing 60, and the exterior of the head portion 86 of the plunger 66 form an expandable sterile chamber 88, preferably having a maximum volume in the range from about 3 ml to about 70 ml, for example 10 ml to 30 ml or 12 ml to 36 ml. The seals 68 at the points of contact between the plunger and the interior wall of the housing are preferably sufficiently airtight that withdrawal of the plunger proximally establishes a partial vacuum within the expandable and compressible sterile chamber 88. In use, withdrawal of the plunger head 86 from the distal portion of the housing in the invention sterile container generates a negative pressure within the sterile chamber 88 and movement of the plunger head from the stops 84 towards the distal end creates a positive pressure on liquids held within the sterile chamber 88.

As shown here, puncturable, self-sealing sterile barrier 64 is an elastomeric septum lodged within opening 62 of the type used to seal and cover the opening of drug vials from which the drug is withdrawn by inserting the needle of a syringe through the septum. A puncture hole in the sterile barrier 64 spontaneously seals itself upon withdrawal of the needle. Thus, the invention sterile container is adapted to receive fluids into the sterile chamber 88 or express fluids from the sterile chamber 88 via a needle (e.g., a hollow needle cannula 76) inserted through the sterile barrier. The proximal end of the sterile container housing 60 is also provided with exterior threads 111 for mating to an invention motorized pressure actuator, or to a syringe.

Figure 2:
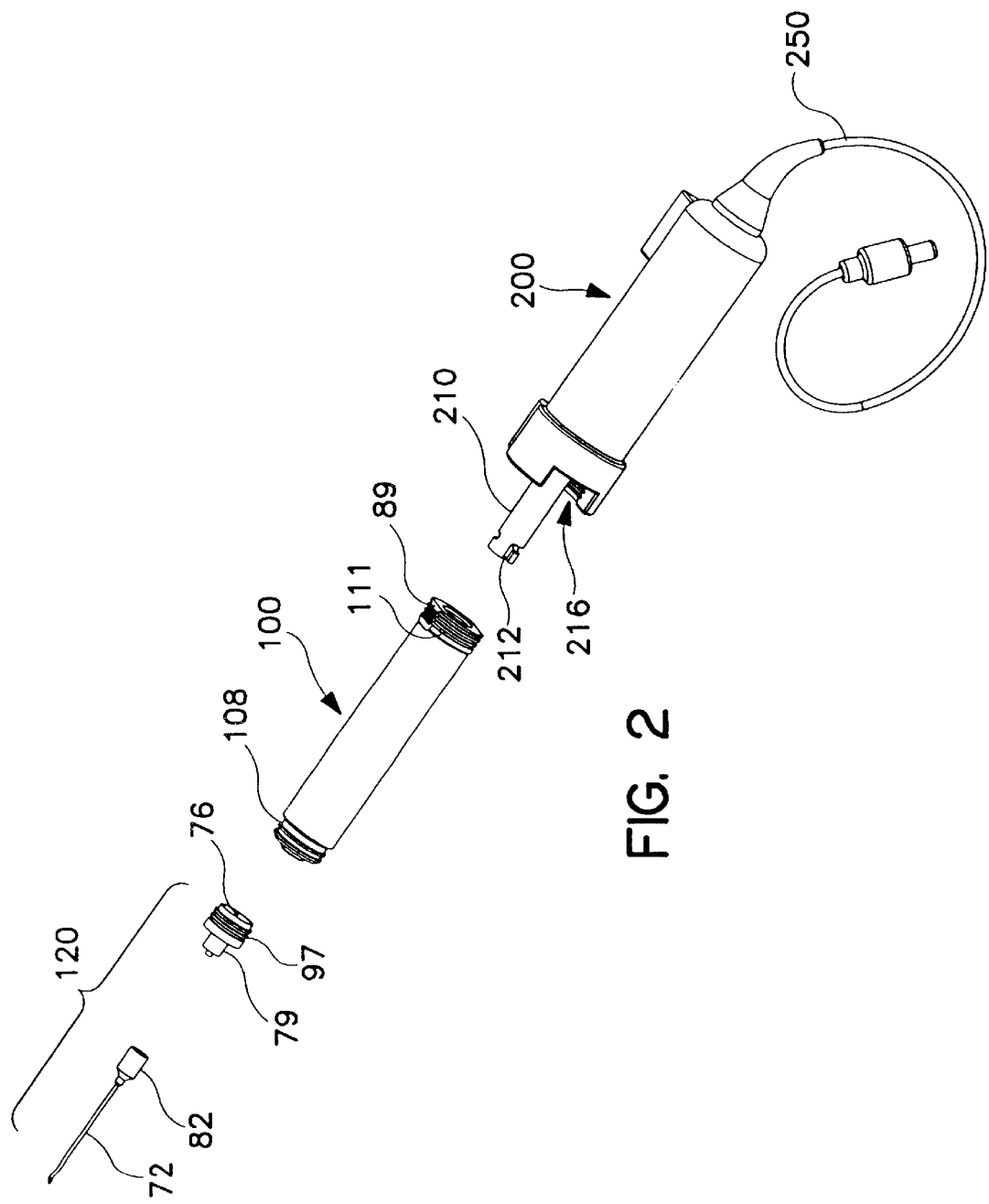
FIG. 2 is a drawing showing an exploded view of an embodiment of the invention injection systems that includes an injection needle, needle adapter for attaching the injection needle to the sterile container, and a motor driven pressure actuator.

As shown in FIG. 2, the sterile container 100 can be assembled with a removably attachable needle adapter 97 that is used to establish fluid-tight connection between the interior of the sterile chamber 88 and a hollow needle 72. Needle adapter 97 has a needle cannula 76 on one side and a fluid connector 79, such as a luer lock or other type of screwing or locking fluid-tight connector, to connect to the hub 82 of a hollow needle 72 on the other side. The proximal portion of the needle adapter 97 may be provided with external threads 110 that threadably mate with internal threads 107 on a lip 108 extending around opening 62 at the distal end of the sterile container 100 to stabilize the connection of the needle adapter to the sterile container during injection. In use, fluids are expressed from the sterile chamber 88 of the sterile container (e.g., through a needle adapter 97 and attached hollow needle 72) by distal movement of the plunger head 86 (e.g., by activation of the pressure activator attached thereto), which exerts a positive mechanical pressure on liquids contained within the sterile chamber 88.

The handle portion 90 of the plunger may extend from the housing 60 so that the operator can grasp the handle portion 90 to move the piston-like plunger by hand. In another embodiment of the invention sterile aspiration/reinjection system shown in FIGS. 2, 4A and 4B, the sterile container 100 can be operably engaged with pressure actuator 200, which moves its piston-like plunger. In this assemblage, the handle portion 90 of the plunger 66 and the distal end of the piston 210 of the pressure actuator 200 cooperatively form a locking mechanism for removable attachment of the plunger 66 to the piston 210 of the pressure actuator 200. For example, as shown in FIG. 1B, handle portion 90 is recessed within the housing 60 of the sterile container and the handle portion is provided with one or more pins or protrusions 104 that engage with an interlocking slot, shown as J-shaped slot 212 located at the distal end of piston 210 of the invention motorized pressure actuator 200. The locking mechanism enables the pressure actuator to move the plunger within the sterile container a precisely controlled distance, or a series of predetermined distances (i.e. incremental movement of the plunger), to expel fluids from the sterile container in a controlled, fixed volume, preferably in the range from about 100 µL to about 2000 µL for each fluid expulsion. Pressure actuator 200 is described in greater detail hereinbelow.

As shown in FIG. 2, the invention also provides a flow through injection assembly comprising a needle adapter 97 that is used to provide fluid-tight connection between the interior of the sterile chamber and a hollow needle 72 with hub 82. Needle adapter 97 has a fluid connector 79, shown as a male Luer lock, to attach to hub 82 on one side and on the opposite end a female fluid connector 79 with recessed needle cannula 76 to provide fluid-tight connection to the interior of the sterile container by thrusting needle cannula 76 through sterile barrier 64.

It is contemplated within the scope of the invention that the injection needle can be straight (as shown) or curved up to about 90 degrees to facilitate injection of fluids into locations difficult to access, such as the epicardium on the backside of the heart. It is also contemplated that the hollow needle used in the injection needle assembly for attachment to the sterile container can be as short as a typical hypodermic needle (as shown) or up to a meter and a half in length. In the latter case, the hollow needle commonly is flexible and is generally threaded through an injection catheter, such as is known in the art, or an injection catheter such as described in copending U.S. application Ser. No. 60/304,607 entitled "DEFLECTABLE TISSUE INJECTION CATHETER WITH CONTROLLED DEPTH PENETRATION," filed on even date herewith.

Figure 3:
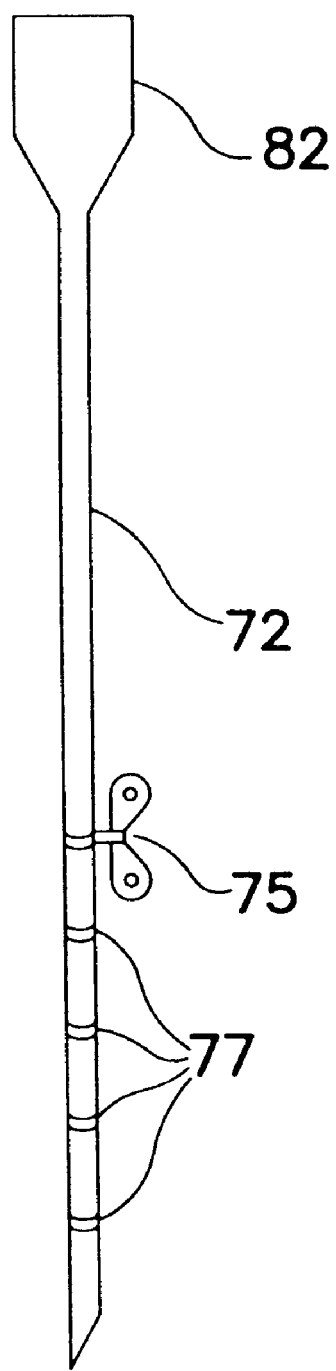
FIG. 3 is a drawing of an invention injection needle for controlled depth penetration

To precisely control the depth of needle penetration during direct injection into an exposed injection site, it is also contemplated within the scope of the invention that the injection needle used in the injection needle assembly is provided with a mechanical stop 75, such as a ring that fits into one or more indentations 77 on the circumference of the needle 72 to prevent penetration of the injection needle to a depth greater than is allowed by the stop, for example 2 mm or 3 mm. As shown in FIG. 3, the exterior of the needle 72 may be provided with a plurality of such circumferential indentations 77 at graduated intervals, for example at 1 mm intervals, and needle stop 75 is a polymer disc with a metal ring surrounding a central opening, with the metal ring being sized to fit into such a circumferential indentation on the exterior of the needle. A tightening mechanism attached to the ring, such as a tightening screw 78, can be used to fixedly seat the metal ring of the needle stop 75 into the circumferential indentation 77 in the needle exterior. If the exterior of the needle is provided with a plurality of such spaced indentations, the position of the stop along the needle and, hence, the depth of penetration of the injection needle, can be adjusted by loosening the tightening mechanism enough to move the stop from one indentation to another and then retightening the tightening mechanism. Alternatively, the shaft of the needle can be graduated in diameter so that indentations along the needle shaft have different diameters. In this embodiment, a plurality of needle stops with central openings sized to seat into the different diameter indentations along the needle shaft are provided.

Figure 4B:
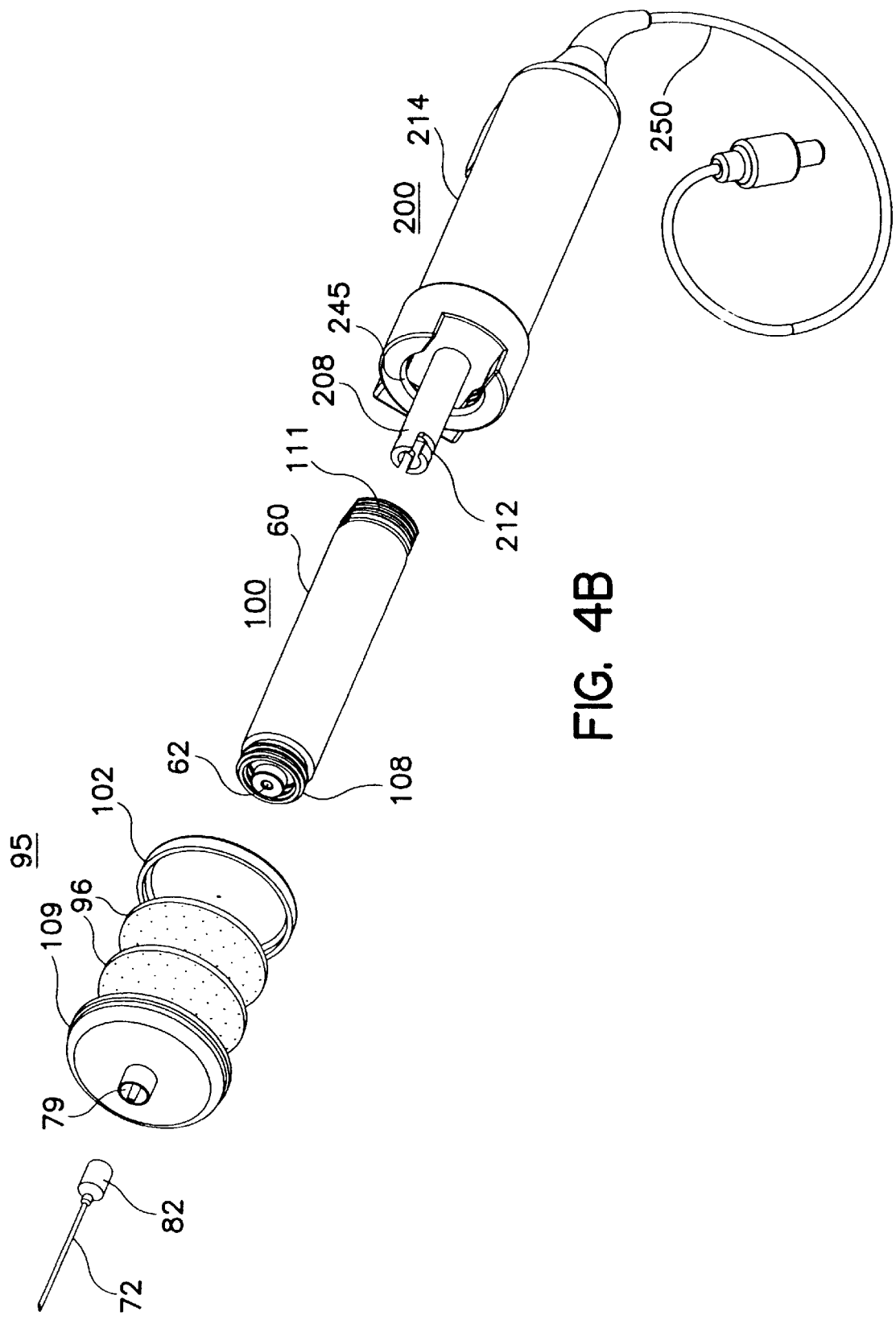

In another embodiment according to the present invention, there is provided a flow-through filter assembly useful for filtering of a bodily fluid containing undesired components, such as, for example, bone marrow aspirate. The invention flow-through filter assembly is useful for filtering fluids collected from a subject to be stored and/or treated in an invention sterile container or for filtering fluids that are being injected into a subject from an invention sterile container. As shown in FIGS. 4A and 4B, the invention flow-through filter assembly 95 comprises a filter receptacle 98 having a distal part 109 and a proximal part 102, which distal and proximal parts releasably engage to cooperatively form a fluid-tight, sterile enclosure for containing two or more replaceable filters 96 with pores sized to filter out undesired components from the fluid passed through the filter assembly. Alternatively, a disposable filter receptacle can be fabricated with the proximal and distal parts bonded together, permanently enclosing the filters inside.

The filters fitted within the filter assembly are generally disk-shaped and the filter assembly can be sized to contain from 1 to about 10 filters, preferably 1 to 3 filters. To avoid clogging of the filter assembly during aspiration of bodily fluids, it is preferred that the distal-most filter has a larger average pore size than the proximal-most filter. For example, when the invention needle assembly is intended for aspiration of bone marrow fluids, the pore size of the filters is selected to filter bone chips (macro-aggregates) from bone marrow aspirate liquids while allowing bone marrow cells and blood cells to pass freely through the filters. Therefore, for this purpose the proximal-most filter may have an average pore size of about 50 microns to about 200 microns and the distal-most filter may have an average pore size of about 200 microns to about 400 microns. In addition, spacers are generally provided between the filters, for example about 0.33 cm to about 0.63 cm spacers, to separate the filters so as to prevent plugging of the filters during use. As shown in FIGS. 4A and 4B, the diameter of the filters can be, and is preferably, many-fold greater than the interior diameter of the needle hub 82, for example 3 to 10-fold larger, to increase the filter surface area, thereby minimizing clogging of the filters. The filters are optionally made of stainless steel. Although any type of filter of appropriate diameter and pore size can be used, Millipore® filters are preferred for their high quality and ready availability.

A male fluid connector 79 on the distal part of the filter receptacle can be used to attach a hollow aspiration or injection needle 72 to the filter assembly 95 in co-axial alignment by connecting to the hub of the needle. A hollow needle cannula 76 mounted on the exterior of the proximal part 102 of the filter receptacle is used to puncture the sterile septum at the distal end of the invention sterile container when the filter assembly is assembled with the sterile container for filtering of fluids expelled from or introduced into the sterile container. It is preferred that the entire filter assembly, with the possible exception of the replaceable filters, is constructed of stainless steel, or a material of comparable strength and stain and heat resistance, so that the invention filter assembly can be sterilized for reuse.

In an embodiment of the invention system shown in FIGS. 4A and 4B, the invention filter assembly 95 is assembled in co-axial arrangement with injection needle 72 by attaching needle hub 82 to fluid connector 79 and piercing sterile barrier 64 of the invention sterile container 100 with needle cannula 76 of filter assembly 95. The sterile container 100, in turn, is operationally connected to an electric motor-driven pressure actuator 200 such that fluids expelled from the sterile container for injection (e.g., by movement of the plunger head from the stop(s) towards the distal end of the container) are filtered before injection into a subject. Alternatively, when the pressure actuator is used to create a negative pressure within the sterile chamber of the sterile container by withdrawal of the plunger head from the distal portion of the housing (i.e., proximally) liquid aspirate can be drawn through the filters in the filter assembly and into the sterile environment of the container. Once the aspirate is received in the sterile container and the needle cannula 76 is removed from the puncturable sterile barrier 64, the self-sealing membrane will spontaneously close the opening made by the needle. Thus, liquids aspirated into the sterile container can be maintained in a substantially sterile condition, stored or treated as desired (e.g., with agents preloaded into the sterile container), and then reinjected into the subject without substantial risk of sepsis.

Figure 5:
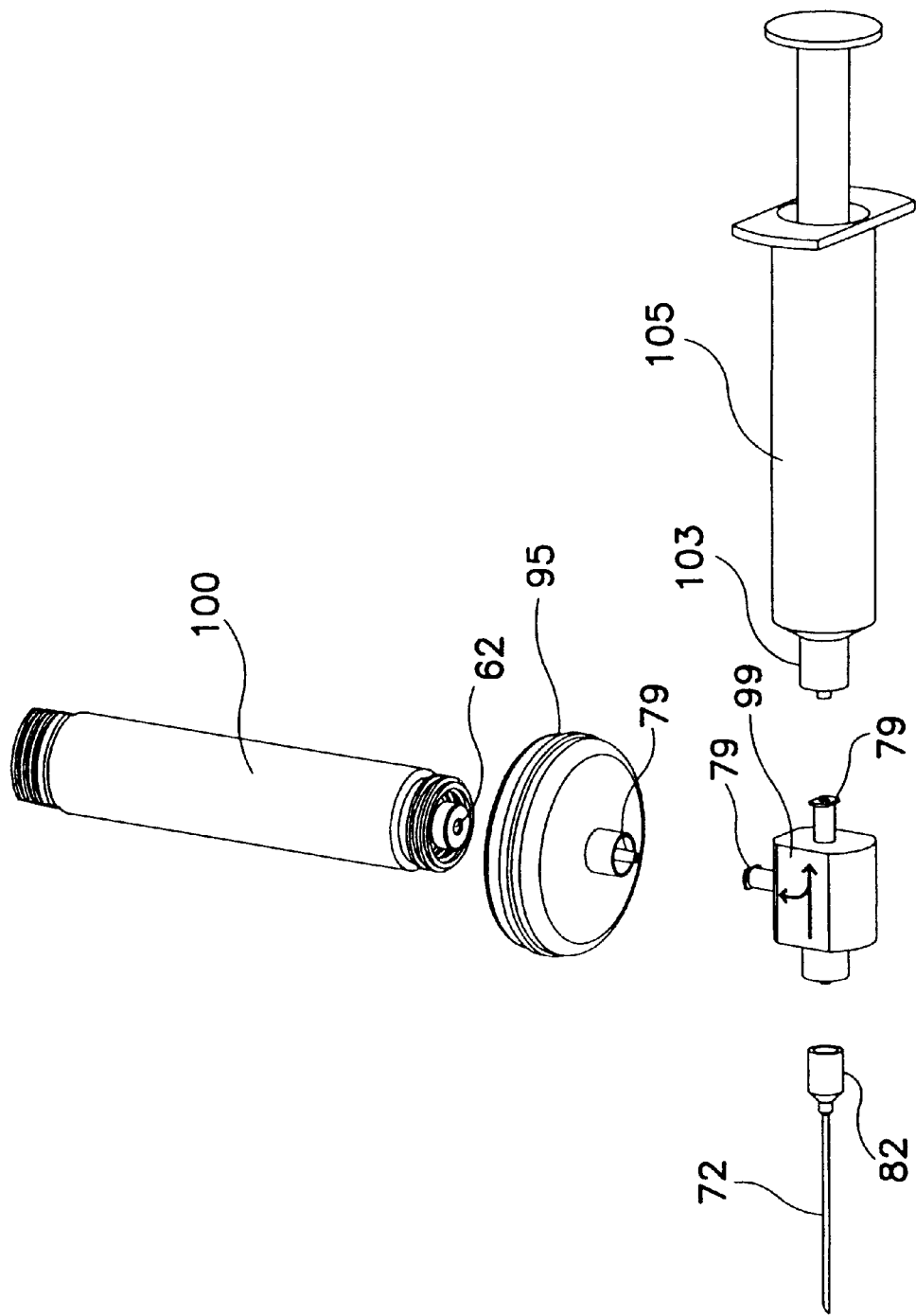
FIG. 5 is an exploded view of an invention aspiration/injection system that includes an assemblage wherein an aspiration needle is attached via a diverter with pressure-activated two-way valve to an aspiration syringe for withdrawal of fluids and to a filter assembly and attached sterile container for receiving withdrawn fluids expressed from the aspiration syringe.

Another embodiment of the invention aspiration/injection system shown in FIG. 5 is intended for use when aspirating fluid from a subject. In this embodiment, the pressure actuator is a conventional suction or aspiration syringe 105 with hub 103, needle 72 is an aspiration needle, and the invention filter assembly 95 and sterile container 100 are not in co-axial arrangement with aspiration needle 72. Instead, a two-way flow diverter 99 interconnects the hub 82 of the aspiration needle 72, a standard sterile surgical aspiration syringe 105, and an invention filter assembly. The aspiration syringe 105 shown is hand-actuated, but can by substituted by an aspiration syringe having an attached motorized suction pump. In this assemblage, the aspiration syringe is used to provide the suction necessary to draw bone marrow fluids from the bone of a subject through the aspiration needle. In this configuration, the filter assembly is further joined in sterile connection to the proximal end of the sterile container by puncture of the sterile barrier with the hollow needle cannula 76 at the proximal end of the filter receptacle 98 so that aspirated fluids contained in the aspiration syringe can be diverted into the sterile container via the filter assembly by actuation of the syringe plunger. The flow diverter 99 and aspiration syringe 105 are co-axially aligned in this assemblage to maximize the suction effect, and the filter assembly 95 and sterile container 100 are arranged at an angle thereto.

The flow diverter 99 houses a two-way fluid valve comprising valves, check valves, petcocks, and the like, with numerous valve configurations yielding the same net effect. The flow diverter is designed to minimize trapped or "dead" volume. Preferably the valving within the flow diverter is pressure-activated such that a negative pressure used in aspiration of fluids directs the aspirated fluids from the needle into the aspiration syringe while a positive pressure (i.e. supplied by compression of the plunger in the aspiration syringe) directs fluids expressed from the syringe through the invention flow-through filter assembly for filtering and into a invention sterile container. For aspiration of bone marrow aspirate, the aspiration needle is preferably constructed of stainless steel and sized for penetrating bone and/or aspiration of bone marrow aspirate fluids, for example from the hip bone or sternum of the donor. For this purpose, a 16-gauge stainless steel needle is preferred.

In yet another hand held assemblage, shown in FIGS. 4A and 4B, injection needle 72, the invention filter assembly 95, the sterile container 100 and the pressure actuator 200 are joined co-axially in fluid communication. This assemblage is particularly adapted for direct injection into an exposed tissue site, such as the epicardium of an exposed heart, for example during a cardiac surgery, such as a cardiac by-pass procedure, wherein at least a portion of the heart surface is exposed. Bone marrow cells can be withdrawn from the sternum of the patient using the invention aspiration device while the chest is open in the early stages of the surgical procedure(s), the cells can be treated as described herein while held in the invention sterile container (e.g., while the anastomosis is performed), and then treated cells can be reinjected into the patient as described herein during the final stages of the ongoing surgical procedure using such a hand held assemblage containing the invention sterile container.

Thus, it is contemplated within the scope of the present invention that the sterile container can itself be contained within or form part of a hand-held injection assemblage for direct injection of fluids into a patient. Alternatively, the sterile container can be contained within a table-top device so that fluids expressed from the sterile container can be injected into a patient percutaneously or via a surgical opening by passing the fluids through an injection tubing, for example up to about 1.5 meters in length, or through an injection catheter. Similarly, the pressure actuator can be located along with the sterile container (and optional filter assembly) in a hand-held device. Alternatively, the pressure actuator (or a part thereof, such as a motorized pump mechanism), can be remotely located from the sterile container, with the pressure being conveyed to the fluid contents of the sterile container by means of a mechanical connection or transducer, a fluid-tight or pressure tubing, and the like.

Figure 6:
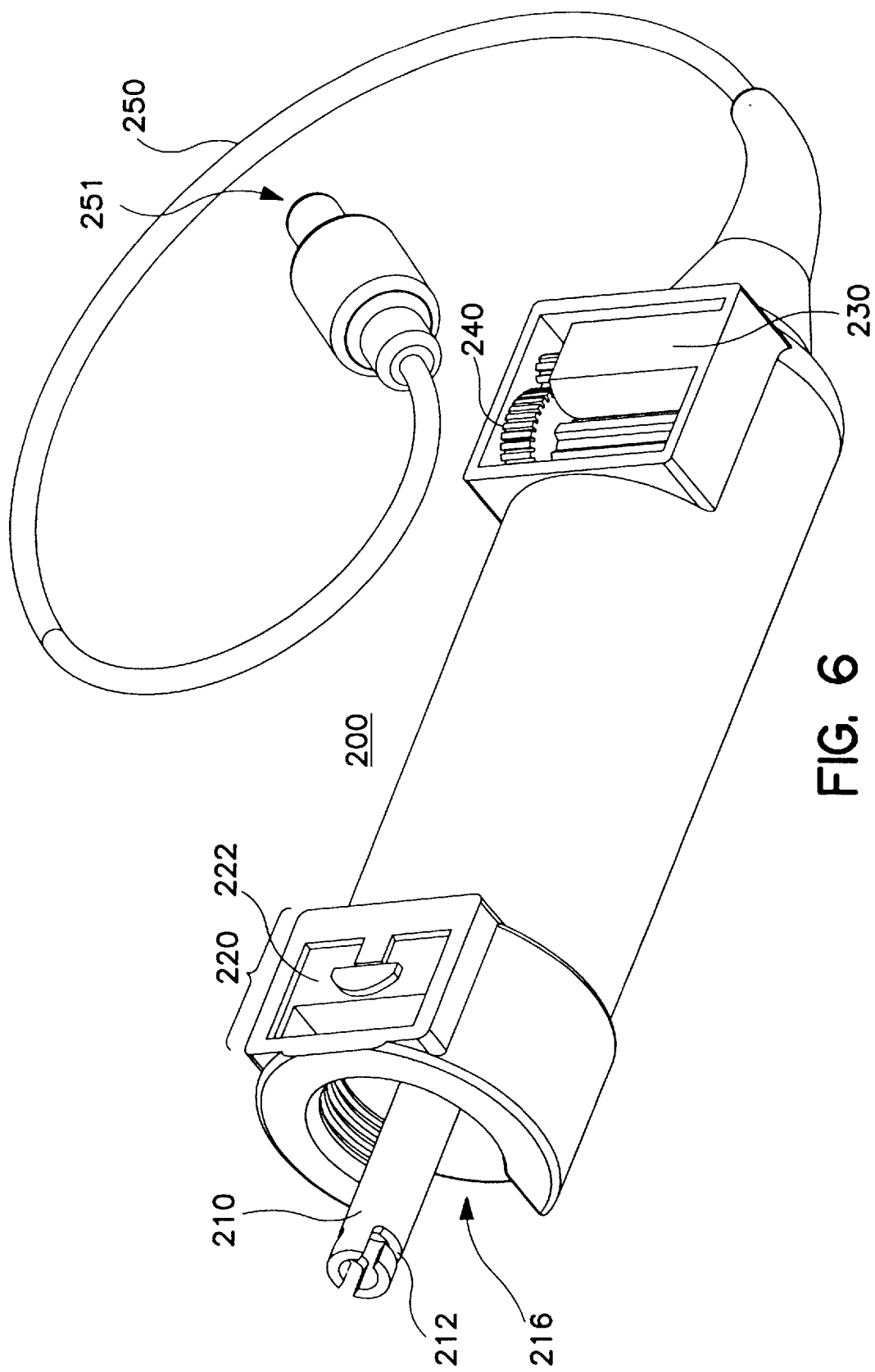
FIG. 6 is a perspective drawing of an invention motor-driven pressure actuator with exterior mounted optical scanner. A reciprocal piston engages mechanically with the plunger of the sterile container.

Pressure actuator 200 can be a motorized pressure actuator, as shown in FIG. 6, having a cylindrical outer housing 214 shaped to receive and couple with the distal end of housing 60 the sterile container and a moveable piston 210 that moves between a withdrawn position and an extended position (as shown in FIG. 6) by operation of a precision motion control motor 230 mounted on the exterior of the housing 214 and mechanically connected to the piston by gear 240. The sterile container and pressure actuator are provided with one or more mechanisms for operationally interlocking so that motion of the actuator plunger is precisely translated to plunger of the sterile container. As described above, one or more pins 104 located on the exterior of the handle portion 90 of the plunger of the sterile container interlock with a J-shaped slot 212 in the distal end of the piston 210 of the pressure actuator. By moving the pin along the vertical portion of the J and twisting the handle portion of the plunger a quarter turn relative to the piston, the pin is forced into and along the transverse bottom of the J so as to engage the locking mechanism.

In this embodiment, the container plunger is recessed completely within the plunger housing. Consequently, engagement of the above-described plunger-piston locking mechanism cannot be visualized. Therefore, to aid in aligning the pin 210 with the top of slot 212, the proximal end of the sterile container and the distal end of the actuator housing are preferably provided with a mating external alignment mechanism that can be visualized during assembly of the invention system components. For example, as shown in FIG. 2, the proximal base of the sterile container 100 is provided with an alignment feature in the form of opposing flat portions 89 on the otherwise cylindrical base of container housing 60 and the proximal end of the actuator housing 214 is provided with mating alignment features, such as alignment cut-outs 216, into which the flat portions 89 of the sterile container are aligned. Once the alignment features are mated, the sterile container is twisted (e.g., a quarter turn) in relation to the pressure actuator to engage interior mating threads 245 with threads 111 provided on the exterior of the container 100. In this embodiment, the alignment features of the alignment mechanism located on the exterior of the sterile container and the pressure actuator are spatially oriented with respect to the plunger-piston interlocking mechanism such that alignment of the flat portions of the sterile container with the cut-outs in the actuator housing positions the pin 104 on the plunger at the top of the slot 212 in the piston. The quarter turn twist of the sterile container with respect to the pressure actuator needed to engage the threads that joint these two devices together also drives the pin into the bottom of the J-shaped slot on the piston, thereby locking the sterile container and pressure actuator together in operable fashion.

The pressure actuator is provided with an actuator mechanism to move the piston between the withdrawn position and extended position so that, when the pressure actuator is mated with the invention sterile container, controlled amounts of fluids held within the compressible sterile chamber of the sterile container can be expelled. As shown in FIG. 6, but not precluding actuation by other means (e.g., linear motor, or "Inchworm" type of piezo-electric driver), the advancement mechanism in the pressure actuator is a precision motion control motor 230 and gear assembly 240 mounted on the housing of the actuator. The precision motion control motor advances a toothed gear in the gear assembly 240, whose teeth fit into grooves provided on the exterior of the actuator piston 210 so as to correspondingly advance the interlocked piston of the actuator and plunger of the sterile container. The precision motion control motor is provided with a source of electrical power, such as an electrical cord 250 for connection to a power source, such as an electrical outlet, battery, solar panel, and the like, via electrical connector 251. The pressure actuator can be provided with a switch or button on the exterior of the actuator that will provide power or signal to actuate the precision motion control motor at will so that timing between actuations is at the will of the operator.

Calibration of the precision motion control motor mechanism relative to the volume of the sterile chamber is such that amounts of fluid expressed from the sterile chamber are minute and rigidly controlled. For example, an amount as small as 0.1 ml to about 2.0 ml is readily expressed through the sterile barrier at the distal end of the sterile chamber by operation of the invention pressure actuator. Those of skill in the art will appreciate that once the physical dimensions (e.g., diameter) of the sterile chamber 88 in the sterile container 100 are known, a correlation between the amount of fluid ejected per expulsion from the sterile container and the distance of travel of piston 210 in the pressure actuator 200 per expulsion is readily calculated.

As shown in FIG. 1A, the sterile container is optionally provided with an indexing feature 218, such as a scan chip with bar code. The indexing feature 218 contains and provides information regarding the contents of the sterile container that can be read by a decoder device contained in or operationally coupled with the pressure actuator, such as a computer in operational communication with the motor. Preferably the indexing feature 218 includes a scanable media or chip containing optically or otherwise recognizable information (e.g., bar code, transponder, or non-volatile memory device) regarding the contents of the sterile container that can be read by a scanner, such as an optical scanner 220, positioned at the distal end of the pressure actuator 200. Preferably the scan chip 218 is located on one of the flat portions 89 at the proximal end of the invention sterile container 100 that functions as the alignment feature. Optical scanner 220 optionally contains a window 222 and is correspondingly positioned on the exterior of pressure actuator 200 such that engagement of the aligning mechanism (and the quarter turn to engage the mating threads between the two components) places the optical scanner 220 in visual alignment with the scan chip 218 (e.g., via window 222) such that the optical scanner can "read" the information on the scan chip. The information "read" by the scanner is then transferred electronically to the motor 230 in the pressure actuator to provide instructions regarding the injection protocol to be executed by the pressure actuator, such as a selected fixed distance the piston in the pressure actuator is to be moved for each increment, the timing of a series of movements, and the like.

Figure 7:
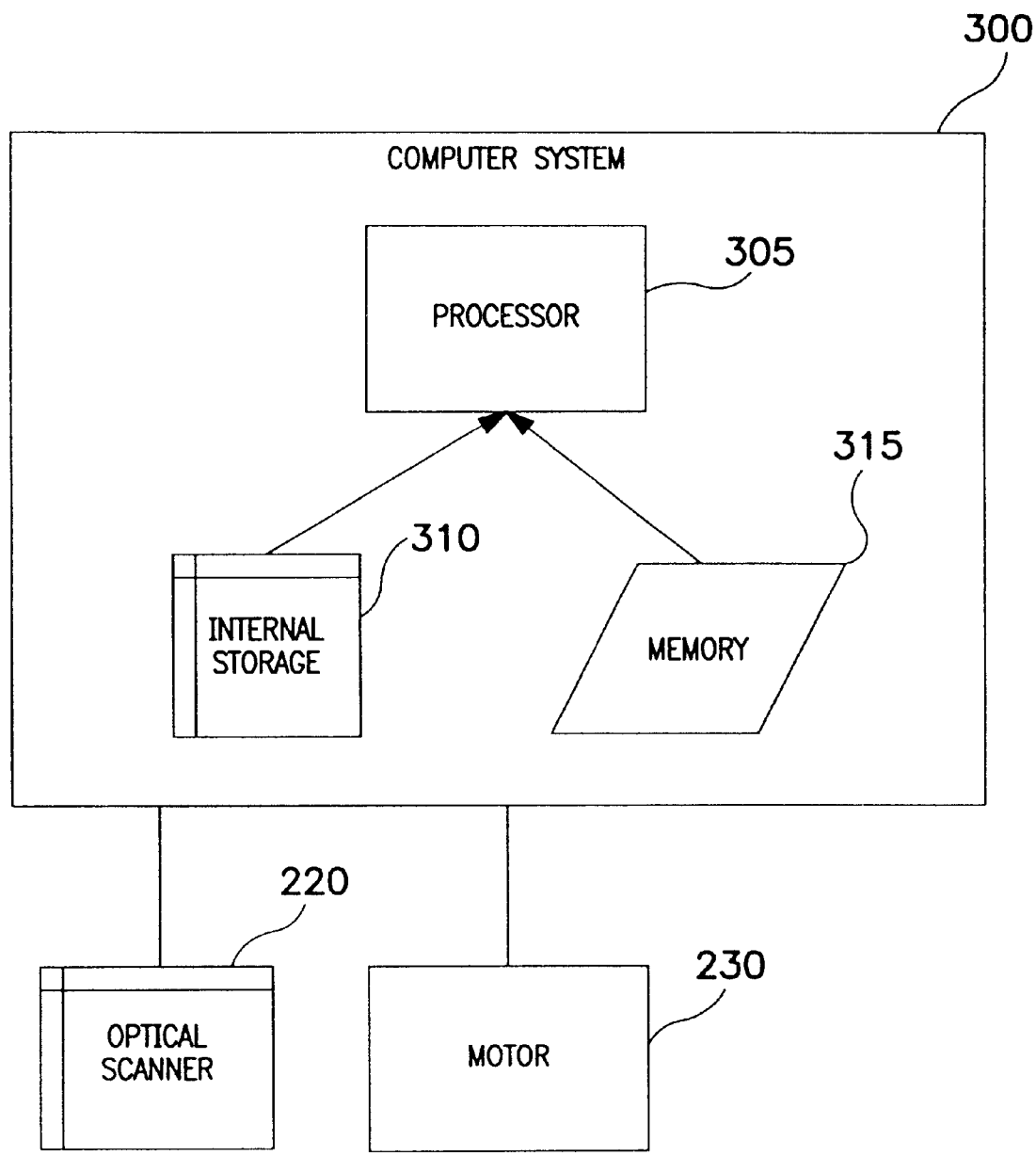
FIG. 7 is schematic drawing illustrating a computer system for use in conjunction with a motor-driven pressure actuator.

In one embodiment, as shown schematically in FIG. 7, the invention system can further comprise a computer system 300 in operational communication with motor 230 and scanner 220. As used herein, "a computer system" refers to the hardware components, software components, and data storage components used to analyze information "read" by optical scanner 220 and translate such information into an impulse, such as an electrical impulse, to motor driver 230. The computer system 300 typically includes a processor 305 for processing, accessing and manipulating the information. Typically computer system 300 comprises a processor 305, internal storage device 310, and memory 315. Information "read" by scanner 220, which includes the amount of liquid to be expressed per dose, number of repeated liquid doses to be expressed, and the like, is received by computer system 300 and computer system 300 translates the received information into instructions to actuate motor driver 230 regarding the distance the piston in the pressure actuator is to be moved forward to accomplish each liquid dose, the timing of a series of such distances (i.e., movements), number of such doses, and the like.

Figure 8:
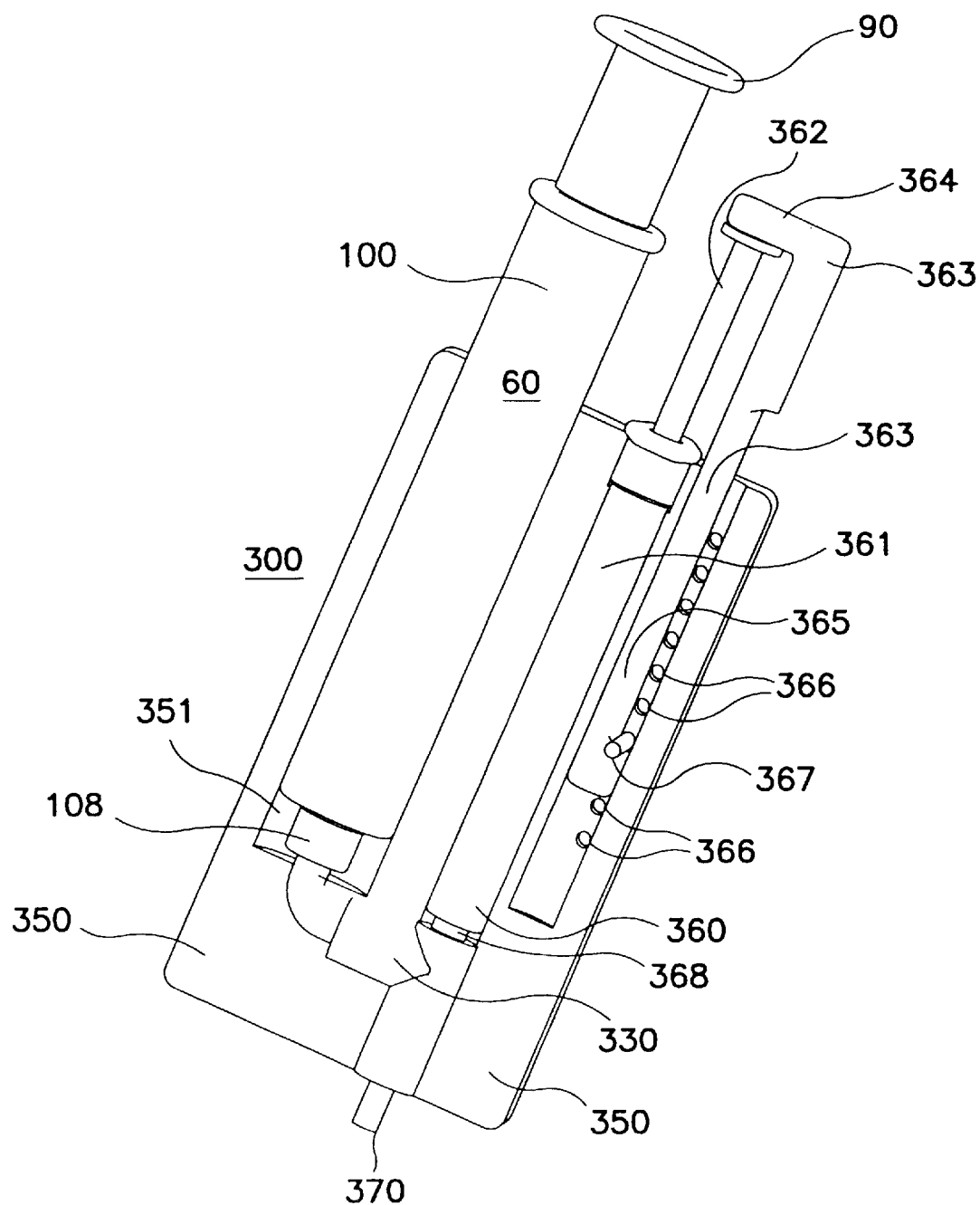
FIG. 8 a top view drawing of an invention hand held injection system comprising an operator-controlled plunger arrester that is manually set by the operator to precisely control the volume of fluid metered into the injection syringe from the invention sterile container and the expressed therefrom by depression of the syringe plunger.
Figure 9:
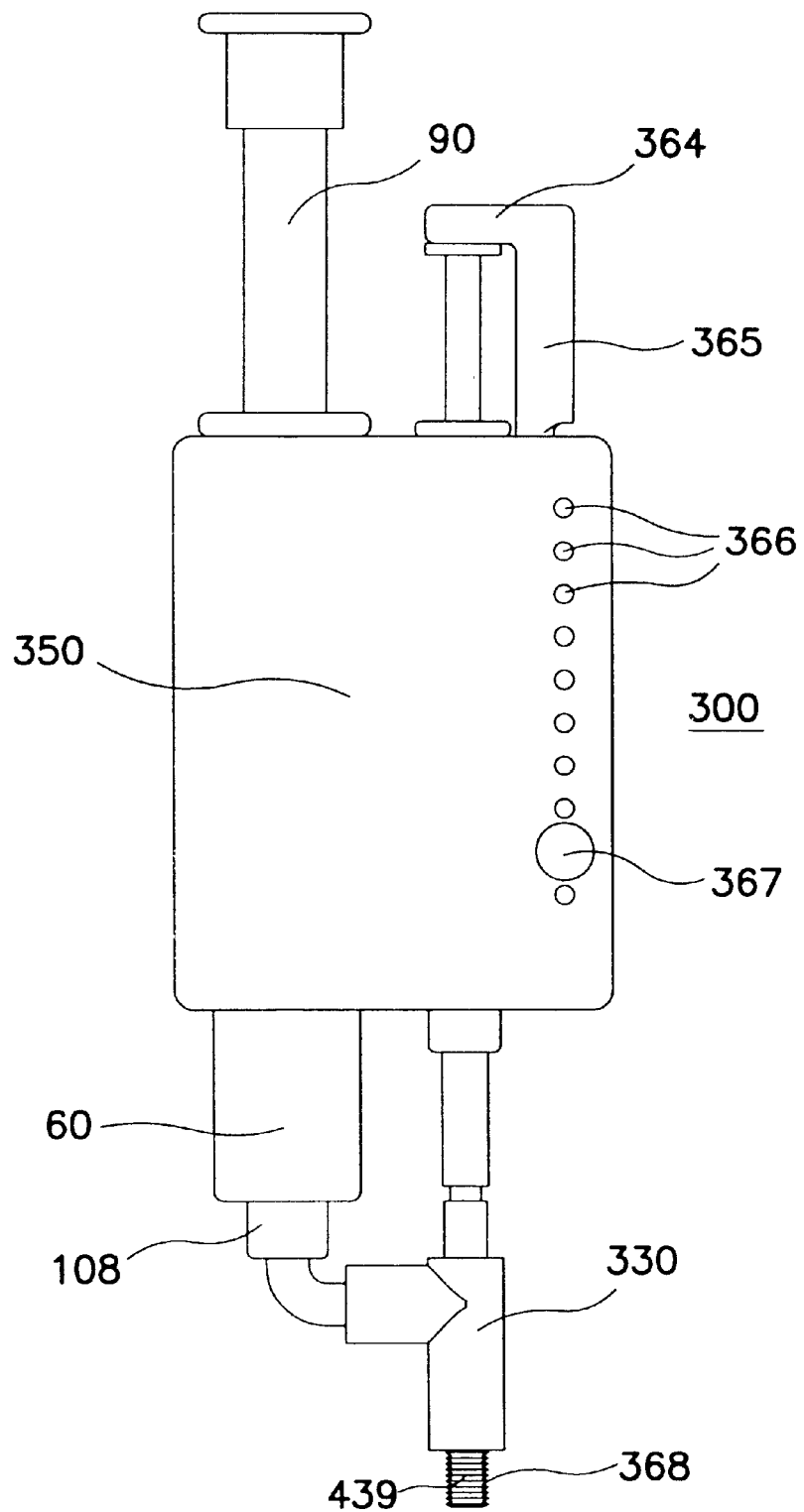
FIG. 9 is a top view drawing of an invention hand-held injection system as show in FIG. 8, but having a holder cover.

In yet another embodiment, the present invention provides a hand-operated injection system for injection of a precisely controlled volume of a therapeutic fluid in a sterile condition. The invention hand-operated injection system is designed to incorporate (e.g. as a drop-in component) the invention sterile container. As shown in FIGS. 8 and 9, this hand-operated embodiment of the invention injection systems comprises in sterile, fluid-tight communication a version of the invention sterile container 100 wherein the pressure actuator is a hand-operated plunger constructed and arranged within the sterile chamber of the sterile container for reciprocal motion within the chamber. Plunger handle portion 90 extends from container housing 60 for hand actuation by the operator. Recessed within lip 108 is an opening into the sterile chamber of the sterile container and a puncturable, self-sealing sterile barrier, as described herein, which covers or plugs the opening to the sterile chamber. The hand-operated injection system further comprises a plunger-operated injection syringe 360 with an elongated barrel 361 having an inner surface defining a fluid chamber and a distal fluid port 368. A syringe plunger 362 is constructed and arranged within the fluid chamber of the syringe for reciprocal motion within the syringe chamber. An adjustable plunger arrester 363 is positioned with respect to the syringe plunger 362 so as to precisely and adjustably control proximal travel of the plunger.

One way liquid flow valves are provided for directing discrete liquid flow from the opening of the sterile container via the puncturable, sterile barrier into the distal fluid port of the syringe and from the fluid port of the syringe into the needle connector. The one way valves can be hand-operated, but are preferably pressure operated such that such that distal compression of the plunger of the sterile container causes liquid to flow only into the fluid chamber of the syringe and only to the extent permitted by the plunger stopper, and wherein distal compression of the syringe plunger expresses liquid contained in the fluid chamber of the syringe only via the needle connector. Preferably, the one way valves are incorporated into a pressure operated three way valve 330 situated in fluid connection (e.g. via fluid connectors (e.g., luer locks, connection tubing, and the like) between the needle connector 370, the distal fluid port 368 of the syringe and the opening of the sterile container 100 via its puncturable, sterile barrier. A fluid connector at the point of fluid connection of the three-way valve and the opening of the sterile container comprises a hollow needle cannula, as described herein, for puncture of the container's sterile barrier. In this configuration, distal compression of handle portion 90 of the sterile container 100 causes one-way flow of liquid only into the syringe's fluid chamber and only to the extent permitted by the syringe arrester 363; while distal compression of the syringe plunger expresses liquid contained within the fluid chamber of the syringe only via the needle connector 370 (i.e., into an attached hollow needle for injection into a subject). Needle connector 370 is designed for attachment of a hollow injection needle, such as a hypodermic injection needle or an injection needle contained in a catheter for percutaneous or epicardial injection of therapeutic fluids into a subject.

The plunger arrester 363 is adjustably positionable with respect to the syringe plunger so as to control proximal travel of the plunger in increments calibrated to expel fixed volumes of fluid from the system. For example, as shown in FIGS. 8 and 9, the adjustable plunger arrester can comprises a moveable plate 365 with an extension 364 positioned so as to contact the proximal end of syringe plunger 362 to limit proximal travel of the syringe plunger. In this configuration, the adjustable positions provided for the plunger arrester allow for increments in proximal travel of the syringe plunger that correspond to virtually any desired increments in expelled fluid, for example 1 mm increments in expelled fluid. For example, in this illustration, position 1 of the plunger arrester could correspond to 0 ml of expelled fluid, position 2 of the plunger arrester could correspond to 1 ml of expelled fluid, position 3 of the plunger arrester could correspond to 3 ml of expelled fluid, and the like. Preferably the adjustable plunger arrester comprises a moveable plate 365 with extension 364 positioned so as to contact the proximal end of syringe plunger 362 to limit proximal travel of the syringe plunger. Those of skill in the art will understand that the plunger arrester mechanism need not be calibrated to result in delivery of equal increments of expelled fluids, or if equal, in ml increments.

The invention hand-held injection system is conveniently contained within a holder 350 sized to be grasped by an adult hand and made of metal or hard plastic, optionally transparent. In this embodiment, as shown in FIG. 8, holder 350 has an interior shape designed to provide a hollow repository 351 into which an invention sterile container is slideably positioned for fluid connection as described above. Thus, the repository space functions as a canister into which the distal end of the sterile container is slideably received. The moveable elongate plate 365 of the plunger arrester can be positioned along side the elongate barrel of the syringe. A series of apertures 366 in holder 350 can be used to adjustably position slideable plate 365 via an arrester pin 367 removably inserted into holder 350 such that proximal movement of the plunger handle is limited while distal movement of the syringe plunger is completely unimpeded. In this embodiment, the increments of expelled fluid are determined by regular spacing of the plurality of apertures, for example, a series of regularly spaced bore holes or slots corresponding to regular increments of expelled fluid.

FIG. 9 shows an enclosed version of the device with holder cover 358 mated with holder 350 so as to enclose the internal components and with pin 367 applied from the exterior of the cover into the apertures in plunger arrester 363

Operation of the invention injection systems takes advantage of the incompressibility of fluids. Depression of the sterile container's plunger handle by the operator forces fluid into the fluid chamber of the syringe via the three-way valve, causing proximal travel of the syringe plunger to the extent allowed by the positioning of the plunger arrester 363. As is typical of injection syringes, the distance of travel of the syringe plunger during injection is calibrated relative to the dimensions of the fluid chamber of the syringe to control the volume of fluid expressed from the syringe via the injection needle attached to needle connector 370.

The invention injection systems are designed to facilitate delivery to a subject of fluid volumes that are minute and rigidly controlled. Thus, when the operator compresses the handle of the sterile container until proximal movement of the syringe handle is stopped, the controlled distance of proximal travel of syringe plunger 362 permitted by the plunger arrester 363 precisely controls the volume of sterile fluid that can be forced into the fluid chamber of the syringe. Similarly, depression of the syringe plunger to the full extent assures delivery of the precisely measured amount of fluid contained in the syringe chamber. To this end, in use, the hollow needle attached to the needle connector 370 is filled with fluid before the plunger arrester is positioned to result in delivery of minute volumes of fluid.

The invention injection systems are also designed to facilitate repeated injection of a fixed volume of sterile fluid into a tissue surface. To this end, it is recommended that the maximum volume of the sterile chamber in the sterile container be at least ten-fold larger than the maximum volume of the fluid chamber in the injection syringe. For example, for injection of sterile bone marrow aspirate from the invention sterile container, the amount of each injection can be about 0.2 ml. If the volume of bone marrow aspirate contained in the sterile container is 10 ml, up to 50 injections having a precise volume of 0.2 ml can be delivered with great accuracy using the invention hand-held device, for example to the epicardium of a heart during by-pass surgery. For this purpose, it is convenient that the maximum volume of the syringe chamber is about 1 ml.

Figure 10:
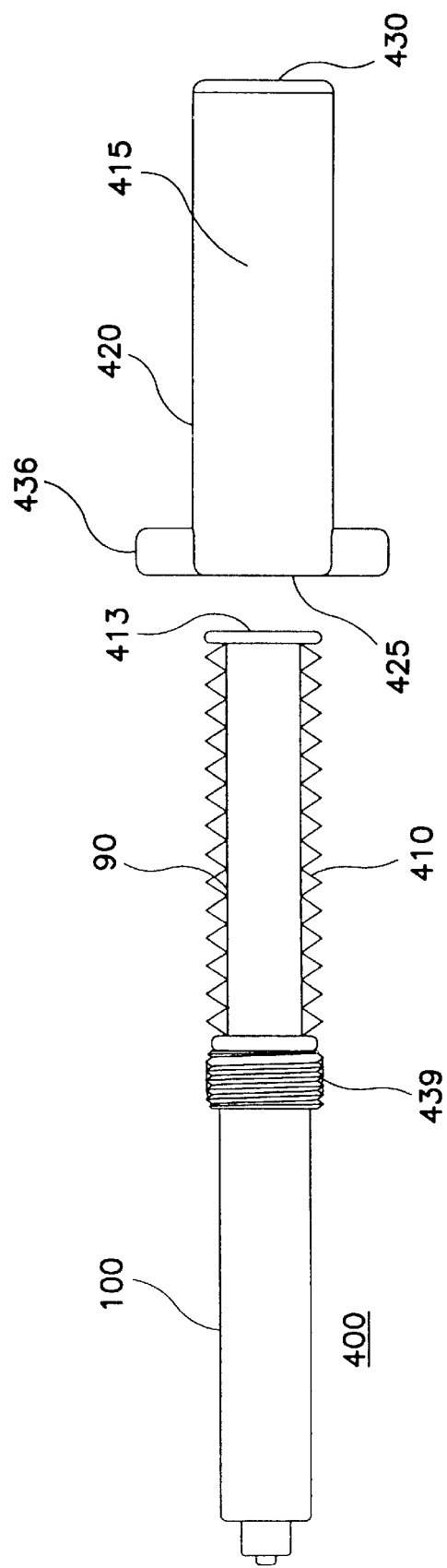
FIG. 10 is a top view drawing of an invention hand-held injection system wherein the plunger of the sterile container is rotatably received within a holder. Rotation of the holder by the operator drives the plunger of the sterile container distally to expel a fixed volume of a fluid contained therein.

Another embodiment of the invention hand-held injection systems is described with respect to FIGS. 10–13 herein. In this embodiment, sterile container 100 has plunger handle 90 extending from the proximal end of housing 60. Fluid-tight seal 410 is moveably mounted on the portion of the plunger handle 90 extending from housing 60 so as to maintain a seal of the fluid chamber upon reciprocal motion of the plunger. As shown in FIGS. 10, 11A and 11B, seal 410 is a pleated bellows sleeve through which plunger handle 90 is inserted, with seal 410 being attached at opposite ends of the exposed plunger handle 90 (but unattached at intermediate points). The pleats of bellows seal 410 compress as plunger handle 60 is driven distally to expel fluids from sterile container 100 while seal 410 provides a continuous barrier to blow-by of liquids from the sterile chamber without restricting reciprocal movement of the plunger handle.

Holder 415, which is a separate component of the injection assembly, comprises an elongated side portion 420, optionally provided with handle portions 436, for grasping by the operator to cause rotation of holder 415 about sterile container 100, distal opening 425, and distal end 430. Holder 415 is fashioned to receive the sterile container plunger-first such that the proximal end 413 of plunger handle 90 abuts against distal end 430 of holder 415 at all times. Rotation of holder 415 about the sterile container progressively advances the sterile container into holder 415 while compressing plunger handle 90 into the sterile chamber so as to expel fluid therefrom. To prevent rotation of the sterile container as the operator rotates the holder about the sterile container, one or more thrust bearings 435 can be located on the interior of the distal end 430 so that the end 413 of the plunger handle abuts against the thrust bearing(s).

Figure 12:
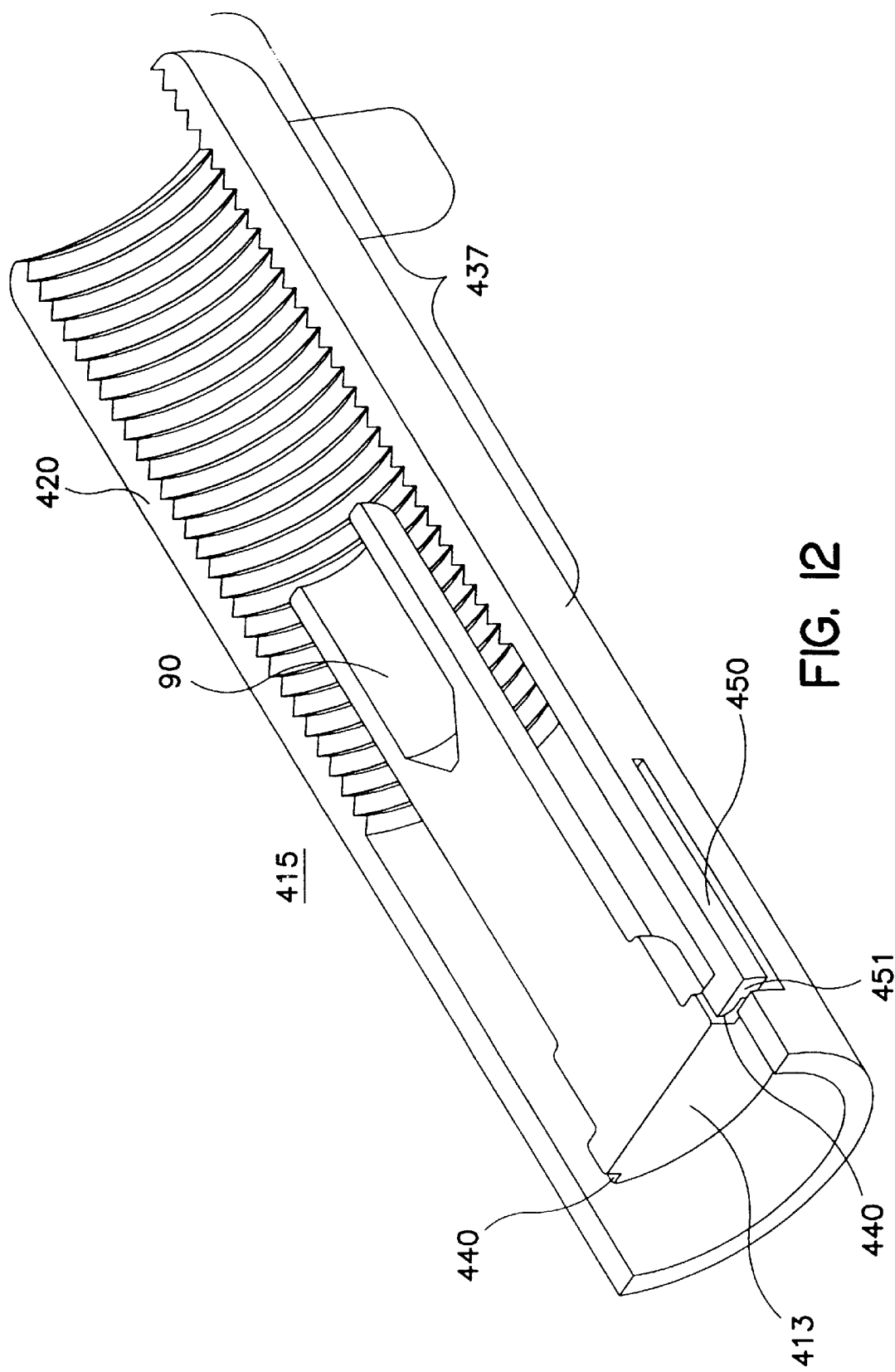
FIG. 12 is a schematic drawing providing a cut-away view of the interior of the holder (with threads) and of the end of the plunger handle so as to show the mechanism for generating an audible and/or tactile signal as the operator rotates the holder about the stationary sterile container.
Figure 13:
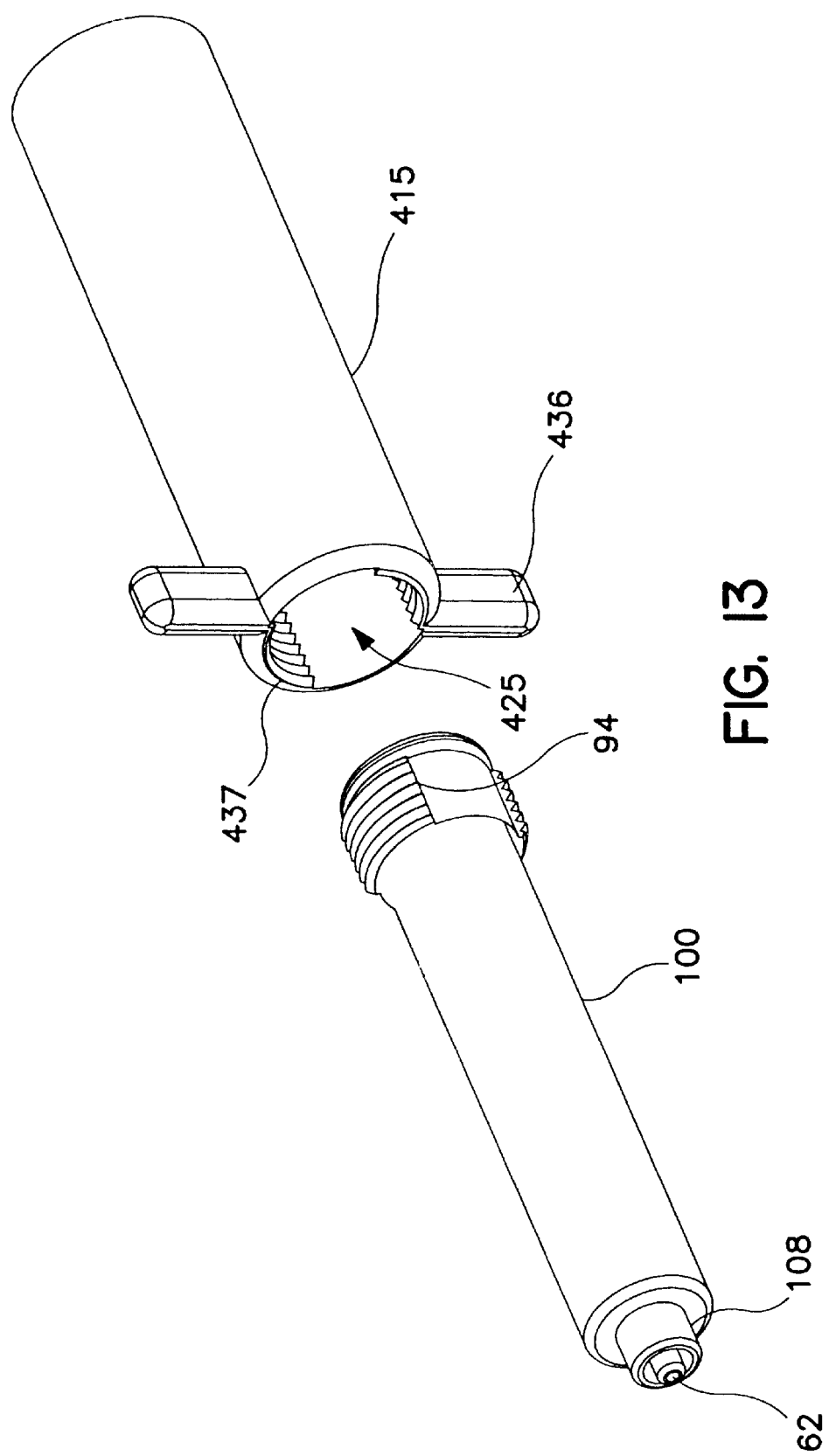
FIG. 13 is a schematic drawing of the hand-held injection system of FIGS. 10–12 wherein the threads on the interior of the holder and those on the exterior of the sterile container housing are interrupted threads.

The mechanism whereby each rotation or partial rotation of the holder about the sterile container causes the plunger to expel a fixed volume of a fluid contained in the sterile container is conveniently one in which each rotation or partial rotation of the holder about the sterile container causes the plunger to advance distally in the sterile chamber a precisely controlled distance. For this purpose, as shown in longitudinal cross-sectional cut away in FIG. 12, threads 437 along the inner surface of the holder 415 rotatably mate with exterior threads 439 on the proximal end portion of the housing 60 so that the proximal end of the sterile container is threaded into the holder much as a nut is threaded onto a bolt. To allow the possibility that the threads can be disengaged to allow a rapid bolus injection (e.g., followed by a series of small controlled volume injections), threads 437 on the interior surface of the holder and mating threads 111 on the proximal exterior of sterile container 100 may each be interrupted threads rather than continuous threads, having at least two sets of thread segments in each with open spaces between. For example, as shown in FIG. 13, there are two sets of 90 degree thread segments 437 with alternating unthreaded 90 degree segments.

As in other embodiments of the invention, the size of the controlled volume of fluid expelled by rotation of the holder about the sterile container is determined by relative sizing of the components of the system. The relation between the distance between adjacent threads on the interior of the holder and the dimensions of the sterile chamber can be selected to expel a desirable volume of fluid from the container per complete revolution or partial revolution. For example, these dimensions can be selected to precisely expel 0.05 ml of fluid per each half revolution and 0.1 ml of fluid per each complete revolution, or 0.1 ml per each half revolution and 0.2 per each complete revolution of the holder about the sterile container, and the like.

A signaling mechanism formed by cooperative interaction of the sterile container and holder during rotation generates a sensible signal (i.e., one that directly addresses one of the operator's senses, such as sight, hearing, touch, or a combination thereof) to advise the operator of how many of the precisely controlled volumes of the fluid have been expelled as a result of the operator causing the rotation of the holder about the sterile container. Thus, the operator has precise control over the volume of fluid injected at each injection site and can readily "measure" the volume of therapeutic fluid injected at an injection site without interruption of the medical procedure.

The sensible signal can be generated in any of a number of ways. For example, a flash of light can be generated by rotation of the injection system momentarily causing an internally mounted LED and miniature battery (e.g., one mounted on the interior of the holder and the other mounted on the exterior of the sterile container) to come into contact. Alternatively, the sensible signal can be audible and/or tactile, such as is generated by a signaling mechanism comprising a detent and ratchet wheel. For example, as shown in FIG. 12, an audible and/or tactile signal is cooperative generated by a ratchet wheel formed from one or more notches 440 in the proximal end 413 of the circular plunger handle 90. Detent 450 comprises a flexible spring-like extension from holder 415 shown as an arcuate flap cut into in the side of holder 415 with a slight protrusion or nub 451 mounted on the interior apex of the flap that will rest within the notch(es) in plunger handle 90. However, those of skill in the art can devise other types of spring-like bodies that will function as a detent, such as a stressed or cantilevered piece or simply a support piece attached to the holder with sufficient flexibility and resilience to function as a spring that will generate an audible signal, such as a clicking noise (and tactile sensation in the hand of the operator) as rotation of the holder with respect to the sterile container causes the detent to move from notch to notch. Or if only one notch is present, the signal will be generated by the detent being forced from the notch and then falling back into the notch upon a complete revolution. Attachment of the detent to holder must provide enough flexibility that the detent does not break when forced out of the notch by rotation of the holder.

In operation, the operator rotates the holder about the stationary sterile container while counting out the requisite number of sensible signals that will correspond to the desired volume of injection for each injection site. For example, a plurality of equal volume injection sites can thus be treated by administering the equal numbers of "clicks" at each injection site as rotation of the holder about the sterile container drives the plunger head distally in the sterile chamber.

The holder is preferably molded or cast from a material, such as a plastic or polymer, with sufficient rigidity that a precision grinder can be used to create the threads 439 with precisely spaced distance between adjacent threads on the interior surface of the holder. However, if the detent is formed from an arcuate flap cut into the side of the holder, the material must not be so rigid as to cause breakage of the detent during use.

The invention hand-operated injection system with sensible signal may further comprise a hollow injection needle in fluid-tight communication with the interior of the sterile chamber, such as a hypodermic needle. Alternatively the hollow injection needle can be contained within an injection catheter.

Figure 14:
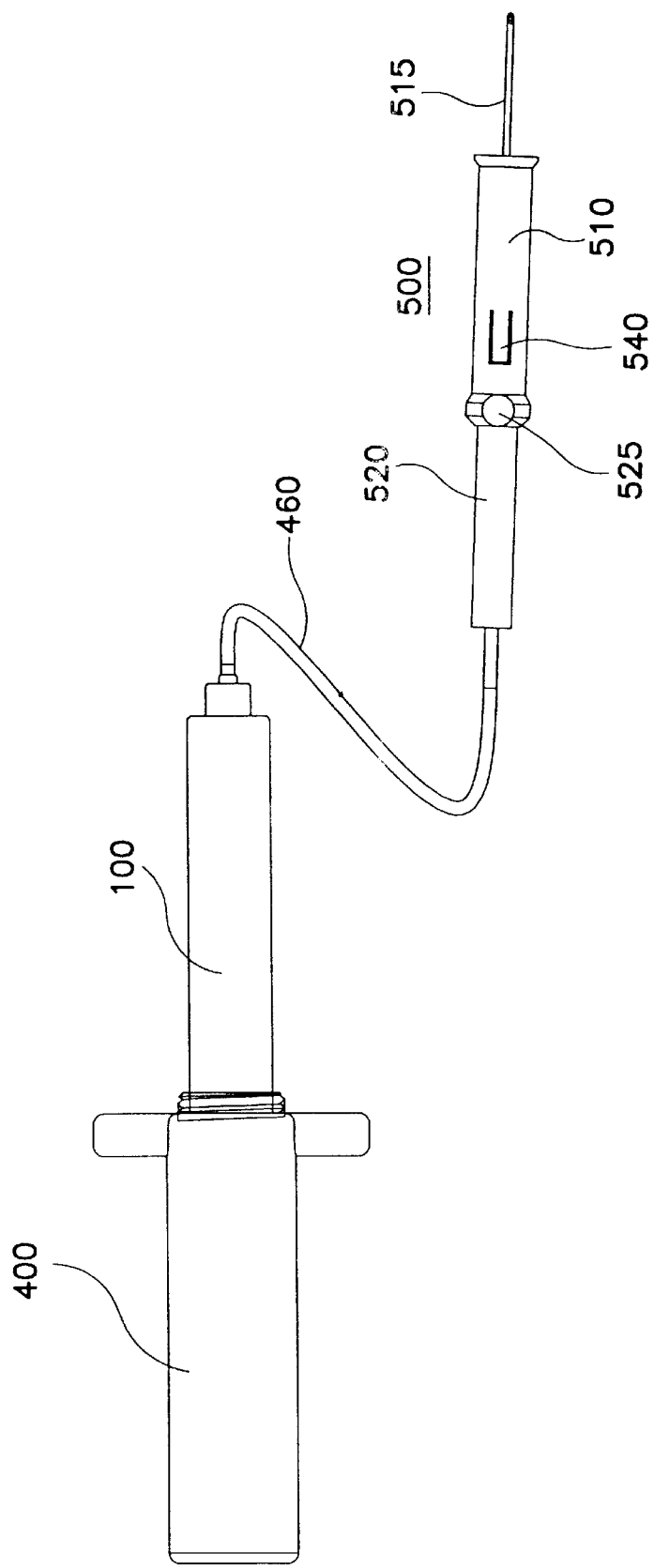
FIG. 14 is a schematic drawing showing an invention hand-held injection assemblage that comprises the system of FIGS. 10–13 attached to an injection catheter with distally attached operator-controlled adjustable needle stop. As one or more precisely controlled increments of the distal tip of the needle are exposed by the operator sliding the needle distally through a series of positions within the needle stop, the needle stop provides a sensible signal to the operator that indicates how many of the precisely controlled increments of the distal tip have been extended from within the needle stop by the operator.

In one embodiment of the invention system shown in FIG. 14, the invention injection system comprises the hand-held system as described above and injection catheter 460 having hollow needle wherein an operator-controlled adjustable needle stop 500 with an indicator showing the length of needle tip advanced is permanently affixed at the protruding distal end of the hollow needle 515 of the injection catheter. The adjustable needle stop that forms a part of the invention injection catheter is designed such that one or more precisely controlled increments of the distal tip of the needle can be exposed by the operator rotating or sliding the needle distally through a series of positions within the needle stop. If the operator slides the needle stop to advance the distal tip of the needle, the needle stop providing an audible and/or tactile signal to the operator that precisely indicates how many of the precisely controlled increments of the distal tip have been extended from within the needle stop by the operator and is fully described in U.S. patent application Ser. No. 10/000,786, filed on even date herewith.

Figure 15:
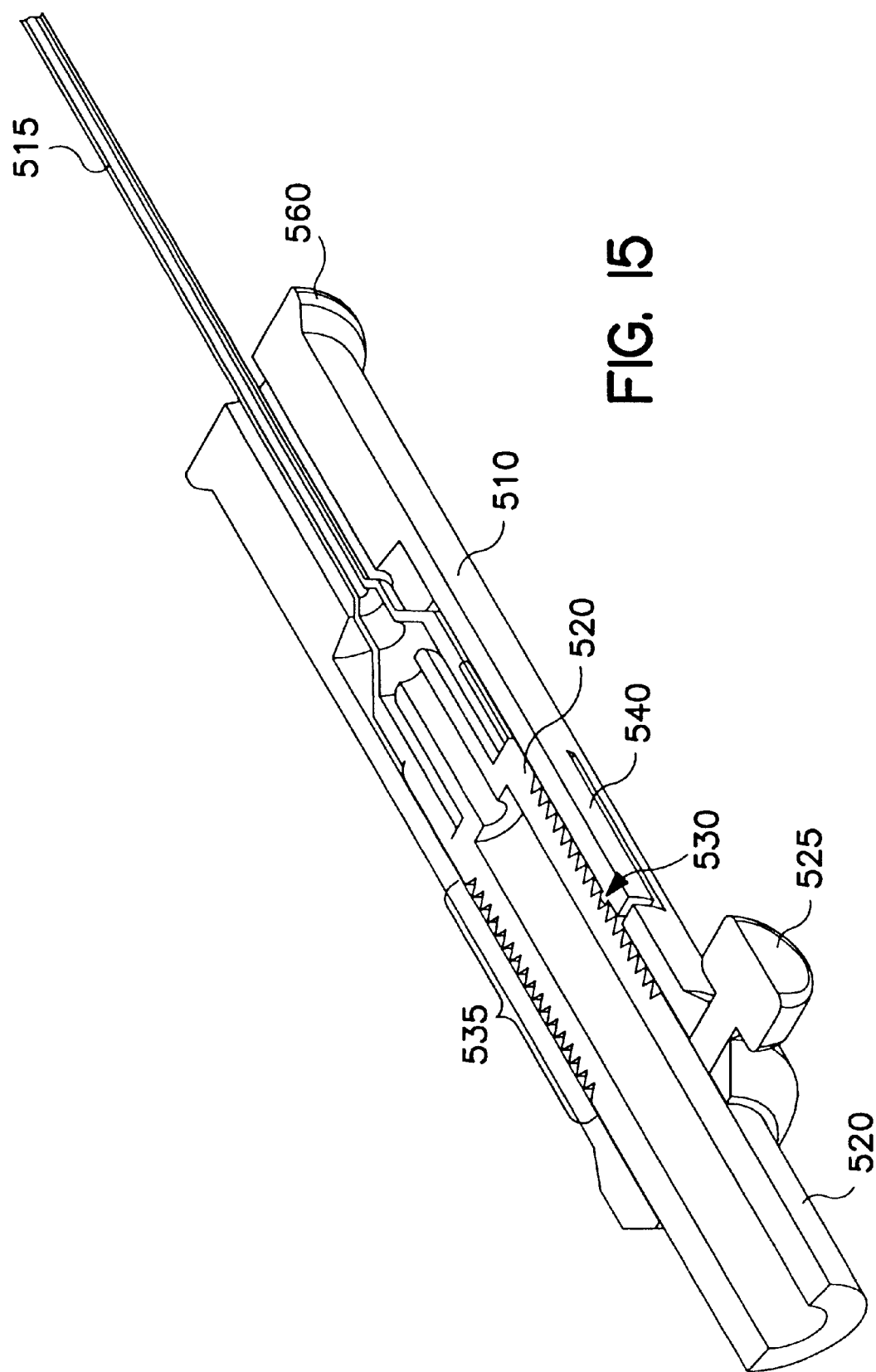
FIG. 15 is a schematic drawing showing a longitudinal cross-section through the operator-controlled adjustable needle stop that is fixedly attached to the end of an injection catheter's injection needle.

In a preferred embodiment, shown in FIGS. 14 and 15, the adjustable needle stop 500 encloses the distal portion of injection needle 515 and comprises in co-axial arrangement a substantially cylindrical outer needle holder 510, and a needle carriage 520 having an interior shaped to receive the distal portion 515 of the injection needle (shown in cut-away) to which the needle carriage is fixedly attached. Preferably, the distal end of the needle holder 510 is bell-shaped with a substantially flat distal end face 560 from which the distal tip of the needle protrudes when the needle is advanced from the recessed position into one of a series of possible advanced positions. The flat distal end face 560 helps to orient the needle orthogonally to the tissue surface for injection.

The needle carriage 520 is mounted within the needle holder 510 for sliding movement or rotation between a fully recessed position, in which the distal tip of the needle does not protrude from the distal end of the needle holder, and a series of progressively advanced positions, in which the distal tip of the needle is progressively advanced to expose the precisely controlled increments of the distal tip thereof. A locking mechanism 525, shown as a tightening screw, is provided for locking the position of the needle carriage with respect to the needle holder during use of the needle for injections.

As shown in longitudinal cross-section in FIG. 15, the mechanism for providing a sensible signal in the invention adjustable needle holder can comprise an internally protruding flexible detent 540 mounted at the proximal end of the outer needle holder 510 and threads 535 (i.e., a series of precisely spaced circumferential "notches") sequentially receive nub 530 on flexible detent 540, causing the detent to move from one thread valley (or "notch") to the next thread valley (or "notch") along the series of threads 535. The needle tip can be advanced proximally in two different ways. The needle carriage 520 to which the needle is fixedly attached can be advanced proximally by rotation of the needle holder 510 about needle carriage 520 while detent 540 rides along threads 535. As indicator of the length of needle tip exposed, calibrated markings can be provided on the exterior of the needle carriage, for example at 0.5 millimeter intervals, by which the operator can visually judge the amount of needle tip that has been exposed by rotation of the needle holder.

Alternatively, needle carriage 520 can be advanced proximally by sliding it within holder 510 such that threads 535 (which function as a series of "notches") sequentially receive nub 530 on flexible detent 540, causing the detent to move from one thread valley ("notch") to the next thread valley ("notch") along the series of threads 535. Sliding the needle proximally as above described emits an audible and/or tactile signal as indicator each time the detent moves from thread valley to thread valley. Thus, in operation the mechanism for generating the audible and/or tactile signal functions in a manner similar to a thumb nail being drawn across the tips of the teeth of a comb.

Preferably, an arcuate cut out flap 540 in the side of the needle holder at the proximal end thereof has an internal protrusion 530 at the apex of the arcuate flap that forms detent 540. In this embodiment, the needle holder is preferably molded or cast from a material, such as a plastic or polymer, having sufficient flexibility that the U-shaped flap with attached detent forms a continuous piece with the body of the needle holder. If the needle carriage is cast or molded, a precision grinder can be used to create the precisely spaced series of notches 535 on the exterior of the needle carriage.

For example, the location of the first thread valley in the series of thread valleys can correspond to the needle being in the fully recessed position and the distance between threads 535 can be precisely controlled such that each audible and/or tactile signal (or "click") caused by advancement of the needle carriage corresponds to one desired increment of needle tip protrusion. For example, if the threads (or "notches") are precisely spaced at 0.5 mm intervals, movement of the needle carriage forward from the fully recessed position sufficient to create 3 signals indicates that the needle tip has been exposed exactly 1.5 mm. Thus, the adjustable needle stop 500 can be designed such that the operator precisely and easily controls the depth to which the needle tip of the invention catheter penetrates a tissue surface for an injection and the operator can readily adjust the depth of needle penetration during a surgical procedure between injection sites by sliding or rotating the needle holder to expose or retract the needle tip, for example by counting a desired number of "clicks."

In use, the invention sterile container is preferably used to receive bodily fluids from a subject donor, which bodily fluids are treated and then reinjected in substantially sterile condition into the subject. For example, the invention sterile container can serve as the reservoir or fluid source from which fluids are provided to an injection catheter for injection of fluids into an interior body cavity, such as the epicardium or myocardium of the heart. When sized for reception of bone marrow aspirate liquids to be treated for reinjection to effect myocardial revascularization, the sterile chamber in the invention sterile container has a volume sufficient to collect and treat enough bone marrow aspirate to inject up to 64 myocardial sites (about 0.2 ml each). In addition, about 0.2 ml of preservative-free heparin per ml of bone marrow aspirate can be added to the bone marrow aspirated into the sterile container to prevent coagulation of the blood therein, making each injection site require about 0.24 ml of injectate. Additional aspirate may be withdrawn to provide sufficient aspirate for microbiological and pathological assessment (about 1 ml) flow cytometry (about 1 ml) and 3–4 ml for additional studies. If the aspirate is to be treated (e.g. by centrifugation) to separate a cellular component (i.e., a mononuclear layer) for injection into the myocardium or epicardium, the amount of bone marrow aspirate withdrawn from the patient will have to be roughly doubled. Accordingly, the volume required for the chamber in the invention sterile container when used for this purpose is in the range from about 6 ml to about 12 ml for 16 injection sites and from about 22 ml to 36 ml for 64 injection sites.

In a preferred embodiment, the chamber of the invention sterile container is preloaded with one or more agents useful for treating or modifying a bodily fluid while the fluid is confined within the sterile chamber For example, when the sterile container is intended to be used for receiving and treating bone marrow aspirate, the chamber can be preloaded with sufficient heparin to prevent coagulation of blood components contained in the bone marrow aspirate. The sterile container can also be preloaded with one or more growth factors or other molecules that promote angiogenesis, such as human vascular endothelial growth factor (VEGF) and/or basic fibroblast growth factor (bFGF), platelet-derived endothelial growth factor (PD-ECGF), endothelial growth factor (EGF), tissue necrosis factor alpha (TNFα), tissue growth factor alpha (TGFα), preferably a growth factor that specifically promotes growth of arteries, such as HIF-1. The sterile container can alternatively be preloaded with a polynucleotide encoding a therapeutic protein, such as any of the above growth factors that promotes angiogenesis or growth of arteries. It is also contemplated that any biologically compatible combination of growth factors and polynucleotides encoding angiogenesis-inducing compounds can be preloaded in the invention sterile container. Information regarding the presence in the container of such above described agents can be registered on or embedded within the scanable media or chip located on the exterior of the invention sterile container to facilitate dosimetric calculations by the pressure actuator.

Preferably a polynucleotide encoding a therapeutic protein will be contained in a delivery system such as is disclosed herein that will promote transfection of cells in the bodily liquid that are introduced into the sterile container, for example blood cells or bone marrow cells. A number of different delivery systems suitable for promoting gene therapy are known in the art that can be used for such purposes. Such transfection of cells can be accomplished within a period of about thirty minutes to two hours.

For example, the one or more polynucleotides encoding one or more therapeutic proteins can be prepackaged in a colloidal dispersion system for delivery into cells held in the sterile chamber. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2–4.0 µm, can encapsulate a substantial percentage of aqueous buffer containing large macromolecules. RNA, DNA and intact virions or can be encapsulated within the aqueous interior and be delivered to cells in a biologically active form (Fraley, et al., *Trends Biochem. Sci.,* 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The polynucleotide encoding the therapeutic protein may be "functionally appended" to, or operatively associated with, a signal sequence that can "transport" the encoded product across the cell membrane. A variety of such signal sequences are known and can be used by those skilled in the art without undue experimentation.

Gene transfer vectors (also referred to as "expression vectors") contemplated for use for such purposes are recombinant nucleic acid molecules that are used to transport nucleic acid into host cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted nucleic acid. Suitable viral vectors for use in gene therapy have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference). Preferred gene transfer vectors are replication-deficient adenovirus carrying the cDNA to effect development of collateral arteries in a subject suffering progressive coronary occlusion (Barr et al., "PCGT Catheter-Based Gene Transfer Into the Heart Using Replication-Deficient Recombinant Adenoviruses," *Journal of Cellular Biochemistry,* Supplement 17D, p. 195, Abstract P101 (March 1993); Barr et al., "Efficient catheter-mediated gene transfer into the heart using replication-defective adenovirus," *Gene Therapy,* vol. 1:51–58 (1994)). In general, the gene of interest is transferred to the heart (or skeletal muscle), including cardiac myocytes (and skeletal myocytes), in vivo and directs constitutive production of the encoded protein. Several different gene transfer approaches are feasible. Preferred is the helper-independent replication deficient human adenovirus 5 system. Using this system, transfection of greater than 60% of myocardial cells in vivo by a single intracoronary injection has been demonstrated (Giordano and Hammond, *Clin. Res.* 42: 123A, 1994).

The recombinant adenoviral vectors based on the human adenovirus 5 (*Virology* 163:614–617, 1988) are missing essential early genes from the adenoviral genome (usually E1A/E1B), and are therefore unable to replicate unless grown in permissive cell lines that provide the missing gene products in trans. In place of the missing adenoviral genomic sequences, a transgene of interest can be cloned and expressed in tissue/cells infected with the replication deficient adenovirus. Although adenovirus-based gene transfer does not result in integration of the transgene into the host genome (less than 0.1% adenovirus-mediated transfections result in transgene incorporation into host DNA), and therefore is not stable, adenoviral vectors can be propagated in high titer and transfect non-replicating cells well.

Retroviral vectors provide stable gene transfer, and high titers are now obtainable via retrovirus pseudotyping (Burns, et al., *Proc Natl Acad Sci (USA)* 90:8033–8037, 1993), but current retroviral vectors are unable to transduce nonreplicating cells efficiently. In addition, the potential hazards of transgene incorporation into host DNA are not warranted if short-term gene transfer is sufficient. In the present invention, a limited duration expression of an angiogenic protein is sufficient for substantial angiogenesis, and transient gene transfer for cardiovascular disease and peripheral disease processes is therapeutically adequate, as is described in U.S. Pat. No. 6,174,871, which is incorporated herein by reference in its entirety.

The amount of exogenous nucleic acid introduced into a host organism, cell or cellular system can be varied by those of skill in the art according to the needs of the individual being treated. For example, when a viral vector is employed to achieve gene transfer, the amount of nucleic acid introduced can be varied by varying the amount of plaque forming units (PFU) of the viral vector.

Those of skill in the art will understand that it may be advantageous to remove excess carrier (especially excess virus) from the treated aspirate prior to injection of the treated aspirate into a subject. For this purpose, yet another assemblage of the invention aspiration/injection system is provided wherein two sterile containers are configured with a flow-through filter assembly positioned between the two sterile containers to provide a sterile wash of the aspirate contained in one of the containers. The size of the pores in the filters used for removing excess carrier will be selected to be large enough for sterile wash fluid, and unreacted remnants of the carrier (such as adenovirus) to pass through the filter(s), but small enough to prevent passage of the treated cells contained in the aspirate, such as stem cells, bone marrow cells, and the like. In this assemblage, the filter assembly is provided with hollow needle cannula 76 attached at the proximal and distal ends of the filter assembly, each of which is used to pierce the sterile barrier of one of the sterile containers. At the start of the wash procedure, the aspirate to be washed will be in the first container and a sterile wash fluid will be contained in the second container. The pressure actuator can be attached to the second container by coupling the actuator piston to the plunger handle of the container. Then the pressure actuator is actuated to force the wash fluid into the first container (e.g., through the flow-through filter assembly). The sterile wash fluid and carrier remnants can then be expressed from the first sterile container by attaching any type of pressure actuator, such as an invention pressure actuator, to the first container and activating the actuator so as to force the wash fluids and carrier remnants through the filter assembly while retaining the treated cells in the first container. The first sterile container containing treated and washed cells is now ready to be injected into a patient by means of an attached pressure actuator using any of the assemblages disclosed herein.

As used herein, the phrase "transcription regulatory region" refers to that portion of a nucleic acid or gene construct that controls the initiation of mRNA transcription. Regulatory regions contemplated for use herein, in the absence of the non-mammalian transactivator, typically comprise at least a minimal promoter in combination with a regulatory element responsive to the ligand/receptor peptide complex. A minimal promoter, when combined with a regulatory element, functions to initiate mRNA transcription in response to a ligand/functional dimer complex. However, transcription will not occur unless the required inducer (ligand therefor) is present. However, as described herein certain of the invention chimeric protein heterodimers activate or repress mRNA transcription even in the absence of ligand for the DNA binding domain.

As used herein, the phrase "operatively associated with" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that transcription of such DNA is initiated from the promoter by an RNA polymerase that specifically recognizes, binds to and transcribes the DNA.

Preferably, the transcription regulatory region further comprises a binding site for ubiquitous transcription factor (s). Such binding sites are preferably positioned between the promoter and the regulatory element. Suitable ubiquitous transcription factors for use herein are well-known in the art and include, for example, Sp1.

Exemplary eukaryotic expression vectors include eukaryotic constructs, such as the pSV-2 gpt system (Mulligan et al., (1979) Nature, 277:108–114); PBLUESKRIPT® vector (Stratagene, La Jolla, Calif.), the expression cloning vector described by Genetics Institute (Science, (1985) 228:810–815), and the like. Each of these plasmid vectors is capable of promoting expression of the protein of interest.

In a specific embodiment, a gene transfer vector contemplated for use herein is a viral vector, such as Adenovirus, adeno-associated virus, a herpes-simplex virus based vector, a synthetic vector for gene therapy, and the like (see, e.g., Suhr et al., Arch. of Neurol. 50:1252–1268, 1993). Preferably, a gene transfer vector employed herein is a retroviral vector. Retroviral vectors contemplated for use herein are gene transfer plasmids that have an expression construct containing an exogenous nucleic acid residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, each of which is hereby incorporated herein by reference, in its entirety. These documents provide a description of methods for efficiently introducing nucleic acids into human cells using such retroviral vectors. Other retroviral vectors include, for example, mouse mammary tumor virus vectors (e.g., Shackleford et al., (1988) PNAS, USA, 85:9655–9659), human immunodeficiency virus (e.g., Naldini et al. (1996) Science 272:165–320), and the like.

Various procedures are also well-known in the art for providing helper cells which produce retroviral vector particles that are essentially free of replicating virus. See, for example, U.S. Pat. No. 4,650,764; Miller, Human Gene Therapy, 1:5–14, 1990; Markowitz, et al., Journal of Virology, 61(4):1120–1124, 1988; Watanabe, et al., Molecular and Cellular Biology, 3(12):2241–2249, 1983; Danos, et al., PNAS, 85:6460–6464, 1988; and Bosselman, et al., Molecular and Cellular Biology, 7(5):1797–1806, 1987, which disclose procedures for producing viral vectors and helper cells that minimize the chances for producing a viral vector that includes a replicating virus.

Recombinant retroviruses suitable for prepackaging with polynucleotides that encode therapeutic proteins, such as angiogenic growth factors, are produced employing well-known methods for producing retroviral virions. See, for example, U.S. Pat. No. 4,650,764; Miller, supra 1990; Markowitz, et al., supra 1988; Watanabe, et al., supra 1983; Danos, et al., PNAS, 85:6460–6464, 1988; and Bosselman, et al., Molecular and Cellular Biology, 7(5):1797–1806, 1987.

The present invention may be embodied in other specific forms without departing from the spirit or central attributes thereof. Thus, the foregoing description of the present invention discloses only exemplary embodiments thereof, and other variations are contemplated as being within the scope of the present invention. Accordingly, the present invention is not limited to the particular embodiments that have been described in detail herein. Rather, reference should be made to the appended claims as indicative of the scope and content of the invention.

What is claimed is:

1. An aspiration/injection system for a bodily liquid containing undesired components, said system comprising the following components:

a) a sterile container comprising in liquid-tight arrangement:
   i) a liquid-tight cylindrical housing with an opening; wherein the interior of the housing is maintained in a sterile condition and has a maximum internal volume in the range of about 3 ml to about 70 ml;
   ii) a self-sealing puncturable sterile barrier covering the opening for receiving a hollow needle cannula, and
   iii) a plunger in liquid-tight co-axial connection with the interior of the housing,
b) a pressure actuator co-axially coupleable to the plunger of the sterile container so that the pressure actuator exerts a positive pressure on the plunger to expel the liquid from the sterile container in a controlled volume by distal movement of the plunger one or more precisely controlled longitudinal distances;
c) a flow-through filter assembly, said filter assembly comprising:
   i) one or more filters with pores sized to filter out undesired components from the liquid and;
   ii) a filter receptacle having at least a distal part and a proximal part, which parts engage to cooperatively form a liquid-tight enclosure for the one or more filters;
   iii) a hollow needle cannula attached to the exterior of the proximal part of the filter receptacle; and
   iv) a liquid-tight liquid connector attached to the exterior of the distal side of the filter receptacle;
e) an aspiration needle with hub for attachment to the fluid connector; and
f) a two way diverter;
wherein components of the system can be operationally coupled in various fluid-tight combinations.

2. The aspiration/injection system of claim 1, wherein the precisely controlled volume is from about 10 ml to about 36 ml.

3. The-aspiration/injection system of claim 1, wherein the sterile container is sufficiently air-tight that the pressure actuator can establish a partial vacuum within the sterile container for aspiration of liquids therein.

4. The aspiration/injection system of claim 1, wherein the pressure actuator comprises a plunger and a seal between the plunger and the housing sufficient to establish a partial vacuum within the housing by withdrawal of the plunger.

5. The aspiration/injection system of claim 1, wherein the pressure actuator applies mechanical pressure to the liquid within the sterile container so as to express the controlled volume of the liquid from the container.

6. The aspiration/injection system of claim 5, wherein the precisely controlled volume is in the range from about 0.1 ml to about 3.0 ml.

7. The aspiration/injection system of claim 1, wherein the sterile container is preloaded to contain one or more agents useful in processing of bone marrow aspirate liquids to enhance the yield of one or more autologous growth factors therefrom.

8. The aspiration/injection system of claim 7, wherein the growth factor is selected from the group consisting of human vascular endothelial growth factor (VEGF), VEGF-2, HIF-1, and basic fibroblast growth factor (bFGF).

9. The aspiration/injection system of claim 1, further comprising a hollow needle for releasable attachment to the liquid connector of the filter assembly.

10. The aspiration/injection system of claim 1, wherein the fluid connector is a male luer connection for releasably attaching the flow-through filter assembly to the hub of a hollow needle.

11. The aspiration/injection system of claim 1, wherein the distal part and the proximal part of the filter receptacle releasably engage by means selected from the group consisting of friction fitting, mating screw threads provided thereon, and luer lock.

12. The aspiration/injection system of claim 1, wherein the distal-most filter has a larger average pore size than the proximal-most filter.

13. The aspiration/injection system of claim 12 wherein the filters are spaced apart to prevent plugging and have average pore openings in the range from about 50 microns to about 300 microns.

14. The aspiration/injection system of claim 1, wherein the diameter of the filters is 3 to 10-fold larger than the interior diameter of the hub.

15. The aspiration/injection system of claim 1, wherein the sterile container-comprises in co-axial arrangement:
   a housing having a cylindrical portion and a distal portion of reduced diameter;
   a distal opening;
   a puncturable, self-sealing sterile barrier covering the distal opening;
   one or more piston ring-like stops fixedly mounted circumferentially around an interior wall of the cylindrical portion of the housing;
   a piston-like plunger having a domed head portion shaped to conform to the interior of the distal end of the housing; wherein the plunger is liquid-tightly and moveably mounted within the cylindrical portion of the housing so that the stroke of the plunger is defined by abutment of the head portion against the distal opening and against a stop; and
   a proximally extending plunger handle for moving the plunger within the cylindrical portion of the housing;
   wherein the sterile barrier, the cylindrical portion of the housing, and the exterior of the domed head portion of the plunger form the sterile chamber and the sterile chamber is expandable and compressible.

16. The aspiration/injection system of claim 15, wherein withdrawal of the plunger head from the distal portion of the housing by the pressure actuator generates a negative pressure within the sterile chamber for aspiration of fluids thereinto and movement of the plunger head from the stop towards the distal end creates a positive pressure on a liquid within the sterile chamber for expelling of the fluids therefrom.

17. The aspiration/injection system of claim 15, wherein the opening at the distal end of the container is surrounded by a protruding lip that is threaded or provides a male luer fitting for attachment to a hollow needle.

18. The aspiration/injection system of claim 15, wherein the stop is provided with a liquid-tight seal between the cylindrical portion of the plunger and the face of each of the one or more piston ring-like stops.

19. The aspiration/injection system of claim 18, wherein the liquid-tight seal is seated in a groove on the face of the one or more stops.

20. The aspiration/injection system of claim 15 wherein the head portion of the plunger has one or more seals circumferentially attached thereto, wherein the seals provide a liquid-tight seal between the interior wall of the housing and the head portion of the plunger.

21. The aspiration/injection system of claim 15 wherein the maximum interior volume of the sterile chamber is in the range from about 12 ml to 36 ml.

22. The aspiration/injection system of claim 15 wherein the sterile container is preloaded with one or more agents for treating or modifying the bodily liquid.

23. The aspiration/injection system of claim 15, wherein the sterile container is preloaded with one or more agents useful in processing of bone marrow aspirate liquids to enhance the yield of one or more autologous growth factors therefrom.

24. The aspiration/injection system of claim 23, wherein the agents are selected from the group consisting of heparin, vascular endothelial growth factor (VEGF), VEGF-2, HIF-1 and basic fibroblast growth factor (bFGF).

25. The aspiration/injection system of claim 23, wherein the one or more agents includes a growth factor that promotes angiogenesis.

26. The aspiration/injection system of claim 23, wherein the one or more agents includes a polynucleotide encoding a therapeutic protein.

27. The aspiration/injection system of claim 26, wherein the polynucleotide encodes a growth factor that promotes angiogenesis.

28. The aspiration/injection system of claim 26, wherein the polynucleotide is contained in a vector for transfection into cells in the liquid for expression of the polynucleotide.

29. The aspiration/injection system of claim 15, wherein the container further comprises a scanable chip on the exterior of the container that provides information regarding the contents of the container that can be read by a suitable scanner.

30. The aspiration/injection system of claim 29, wherein the scanable chip contains information regarding the contents of the sterile container that can be read by an optical scanner.

31. The aspiration/injection system of claim 30 wherein the scanable chip is an optically scanable bar code and the exterior of the pressure actuator further comprises an optical scanner positioned thereon such that operational coupling of the sterile container and the pressure actuator places the optical scanner in visual alignment with the scan chip.

32. The aspiration/injection system of claim 30, wherein information read by the scanner is transferred electronically to the motor in the pressure actuator so as to selectively control the precisely controlled distance the motor moves the container plunger.

33. The aspiration/injection system of claim 23, wherein the exterior of the container has an optical scan chip that provides information regarding the one or more agents preloaded into the container.

34. The aspiration/injection system of claim 33, wherein the scan chip contains visible barcode information concerning the modifying or treating of bodily liquids introduced into the container.

35. The aspiration/injection system of claim 1, wherein the system is configured as a hand-held device.

36. The aspiration/injection system of claim 1 wherein the pressure actuator further comprises a motor that repeatedly exerts the positive pressure on liquid in the sterile container by operational attachment to and movement of the the plunger a precisely controlled longitudinal distance.

37. The aspiration/injection system of claim 36, wherein the precisely controlled distance is calibrated to expel a fixed volume of liquid in the range from about 100 $\mu$L to about 2000 $\mu$L from the sterile chamber.

38. The aspiration/injection system of claim 36 wherein the motor is a precision motion control motor.

39. The aspiration/injection system of claim 38, wherein the precision motion control motor is operator-controlled.

40. The aspiration/injection system of claim 36 wherein the proximal end of the sterile container and the distal end of the actuator contain mating parts of an alignment mechanism to facilitate operational coupling of the plunger of the sterile container to the pressure actuator.

41. The aspiration/injection system of claim 40, wherein the pressure actuator comprises a piston co-axially housed within a cylindrical housing and the container plunger can be operationally coupled with the distal end of the piston such that the motor drives the piston the predetermined proximal distance within the pressure actuator housing.

42. The aspiration/injection system of claim 41, wherein one or more pins located on the exterior of the plunger handle and a J-shaped slot in the distal end of the pressure actuator piston cooperate to form an operational coupling mechanism for coupling a plunger handle and the piston.

43. The aspiration/injection system of claim 41, wherein the sterile container and the pressure actuator each further comprises an exterior interlocking alignment feature for operational coupling thereof.

44. The aspiration/injection system of claim 36, wherein the system further comprises:

a computer system for assembly in operational communication with the precision motion control motor for actuating the motor so as to expel the fixed volume of liquid from the sterile container.

45. The aspiration/injection system of claim 1 further comprising:

e) an aspiration syringe with moveable plunger, which can be operationally coupled with the hub of the aspiration needle; and f) a three-way diverter;

wherein the needle cannula of the filter assembly can puncture the sterile septum of the sterile container and wherein the three way flow diverter can be operationally coupled to divert liquids aspirated through the aspiration needle into the syringe and to divert liquids ejected from the syringe into the sterile container through the flow-through filter assembly.

* * * * *